(12) United States Patent
Johnson et al.

(10) Patent No.: US 12,396,880 B2
(45) Date of Patent: Aug. 26, 2025

(54) OSTOMY OUTPUT DIVERSION DEVICE

(71) Applicants: Bruce M Johnson, Simpsonville, SC (US); Theresa G Johnson, Simpsonville, SC (US); Reed B Johnson, Greenville, SC (US); Ashley Davis, Cumming, GA (US)

(72) Inventors: Bruce M Johnson, Simpsonville, SC (US); Theresa G Johnson, Simpsonville, SC (US); Reed B Johnson, Greenville, SC (US); Ashley Davis, Cumming, GA (US)

( * ) Notice: Subject to any disclaimer, the term of this patent is extended or adjusted under 35 U.S.C. 154(b) by 459 days.

(21) Appl. No.: 18/052,650

(22) Filed: Nov. 4, 2022

(65) Prior Publication Data

US 2023/0083546 A1    Mar. 16, 2023

Related U.S. Application Data

(63) Continuation-in-part of application No. 16/679,960, filed on Nov. 11, 2019, now Pat. No. 11,504,264, which is a continuation-in-part of application No. 16/518,506, filed on Jul. 22, 2019, now Pat. No. 11,564,827.

(51) Int. Cl.
*A61F 5/448* (2006.01)
*A61F 5/449* (2006.01)

(52) U.S. Cl.
CPC .............. *A61F 5/448* (2013.01); *A61F 5/449* (2013.01)

(58) Field of Classification Search
CPC ........ A61F 5/445; A61F 5/4404; A61F 5/448; A61F 5/449; A61F 5/44
See application file for complete search history.

(56) References Cited

U.S. PATENT DOCUMENTS

| | | |
|---|---|---|
| 1,256,857 A | 2/1918 | Wofford |
| 2,314,724 A | 3/1943 | Marsan |
| 2,528,227 A | 10/1950 | Johnson |
| 2,536,036 A | 1/1951 | Cloninger |
| 3,367,338 A | 2/1968 | Crandall |

(Continued)

FOREIGN PATENT DOCUMENTS

| | | |
|---|---|---|
| CN | 107468406 | 12/2017 |
| GB | 5449 | 11/1906 |

(Continued)

*Primary Examiner* — Kai H Weng
(74) *Attorney, Agent, or Firm* — Thomas L. Moses; Southeast IP Group, LLC.

(57) ABSTRACT

An ostomy output diversion device is used to cover and seal closely around a patient's stoma, to divert stoma effluent output through the device, into a container or reservoir, temporarily eliminating the need of an adhesive-based ostomy pouching system. The ostomy output diversion device is placed over the person's stoma, with the base ring surrounding the peristomal skin, the adjustable inner tube is retracted until the base ring is centered over the stoma, the body support strap is then placed over the device to secure it to the patient's body, the inner tube is then extended over the stoma, the patient applies the desired pressure against the skin, then secures the inner tube in place with the pressure adjustment lock. The device may also include an ostomy pouch mounting ring for attachment to an ostomy pouch, and a disposable receptacle.

4 Claims, 26 Drawing Sheets

(56) References Cited

U.S. PATENT DOCUMENTS

| | | |
|---|---|---|
| 3,577,982 A | 5/1971 | La Par |
| 4,296,749 A | 10/1981 | Pontifex |
| 4,723,952 A | 2/1988 | Esposito |
| 5,125,916 A | 6/1992 | Panebianco et al. |
| 5,503,625 A | 4/1996 | Plass |
| 2013/0030397 A1* | 1/2013 | Sabeti ................ A61F 5/4405 604/338 |
| 2016/0287428 A1 | 10/2016 | Eggert et al. |
| 2019/0060104 A1 | 2/2019 | Cesa et al. |

FOREIGN PATENT DOCUMENTS

| | | |
|---|---|---|
| KR | 20170008000 | 1/2017 |
| WO | WO0100260 A1 | 1/2001 |

\* cited by examiner

- Fig. 1 -
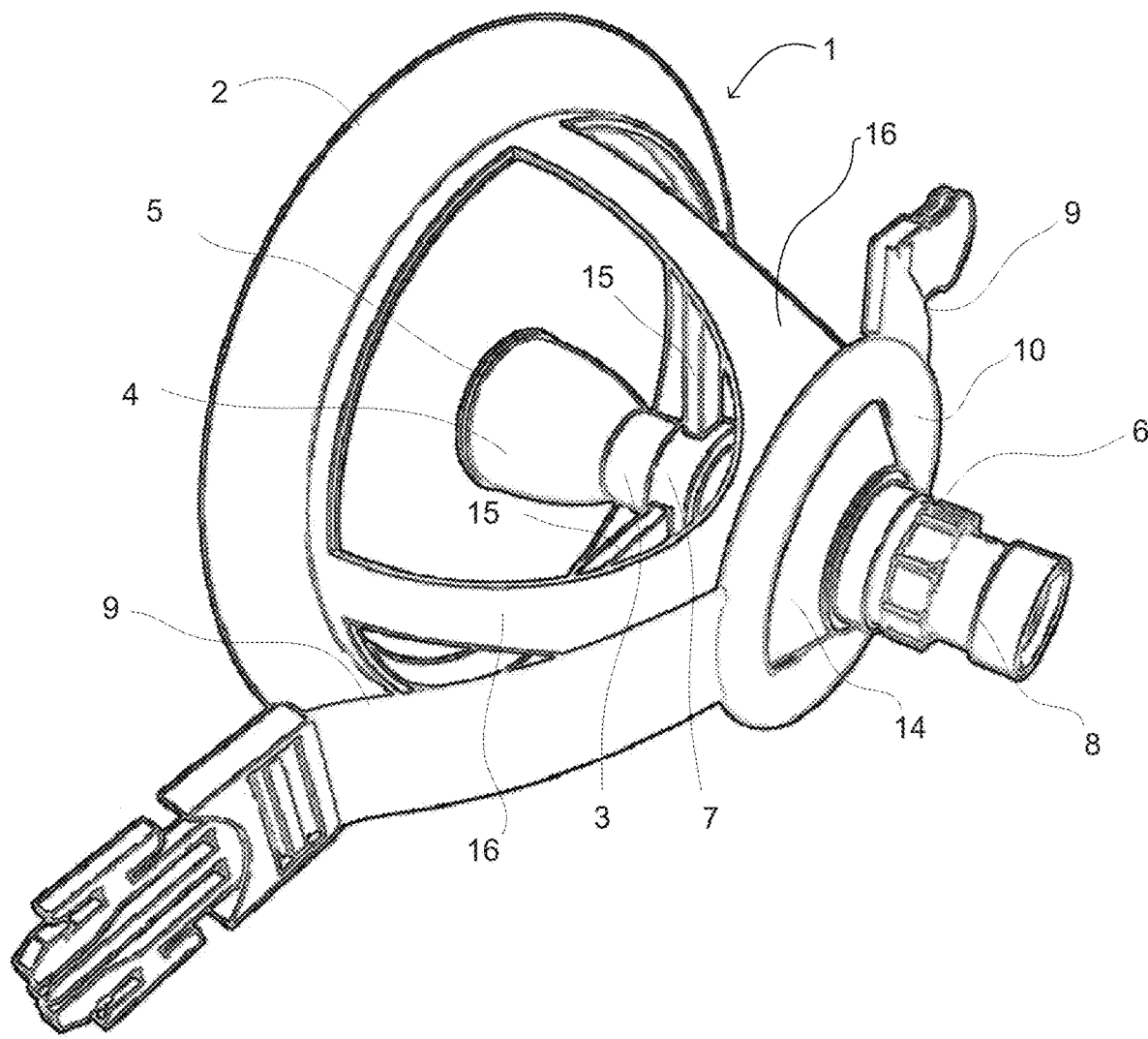

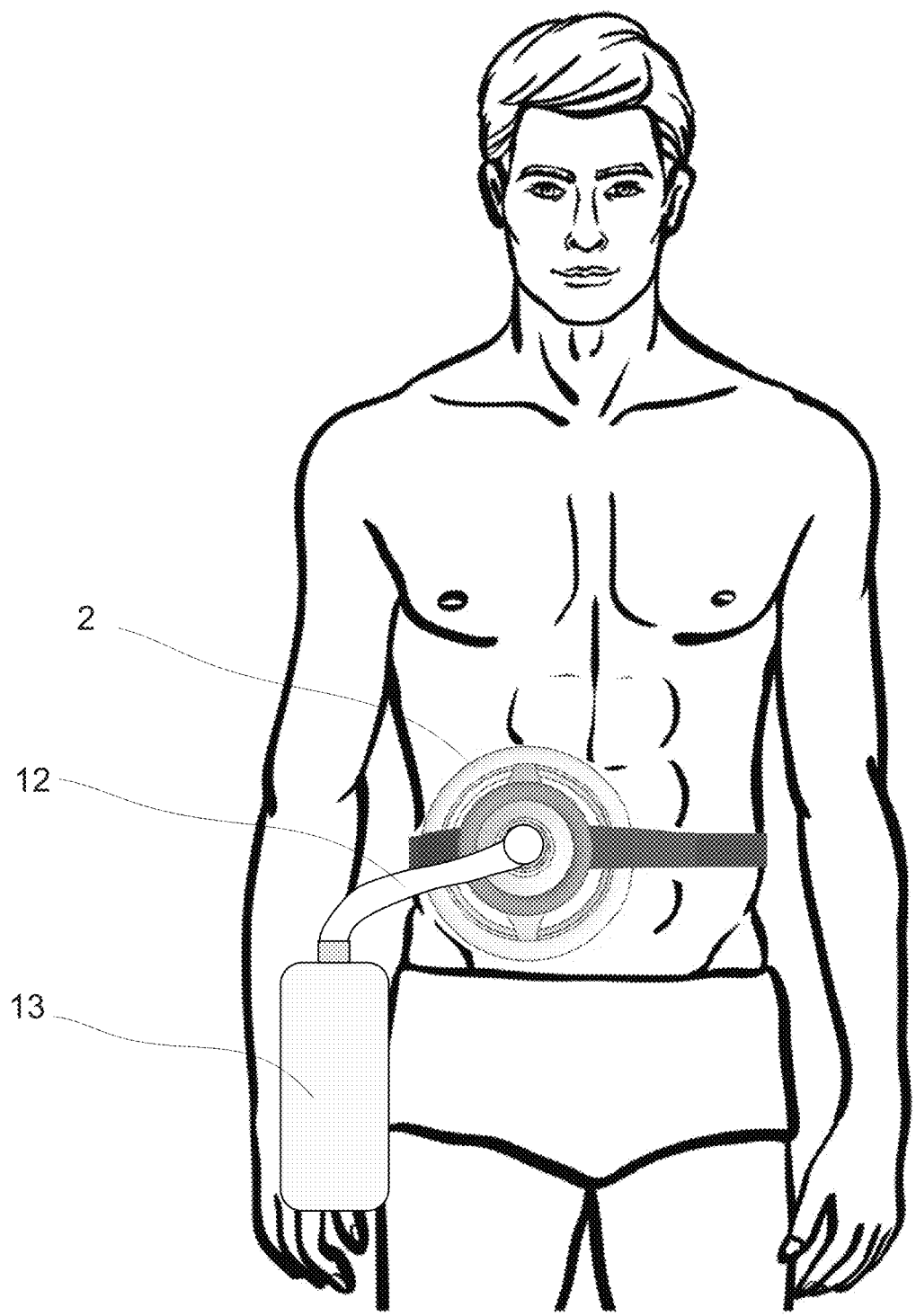
- Fig. 2 -

Fig. - 3A -
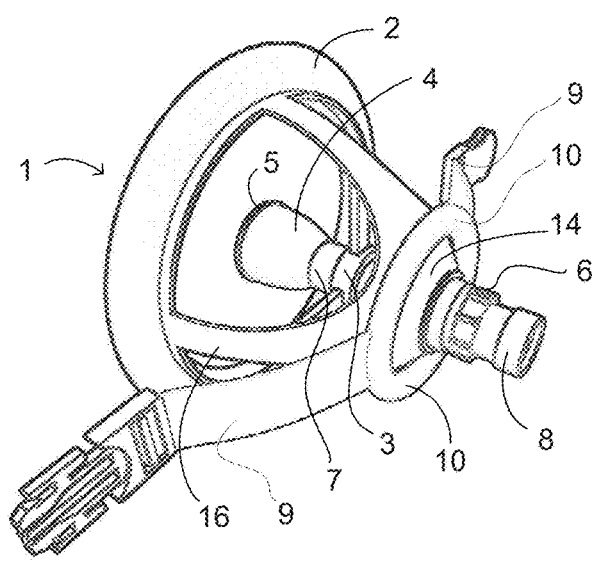
Fig. - 3B -
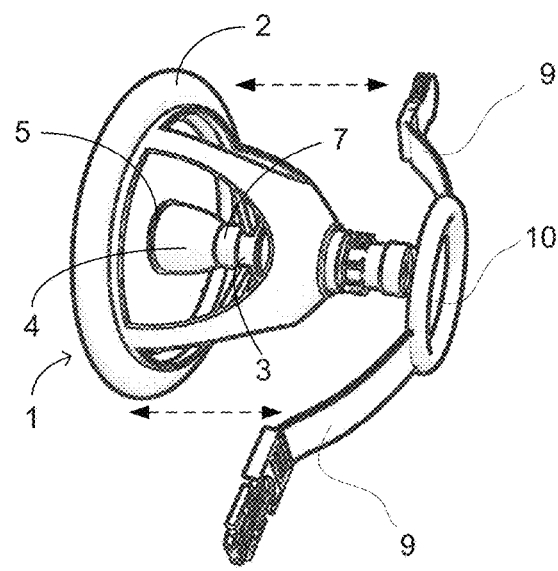

- Fig. 4 -
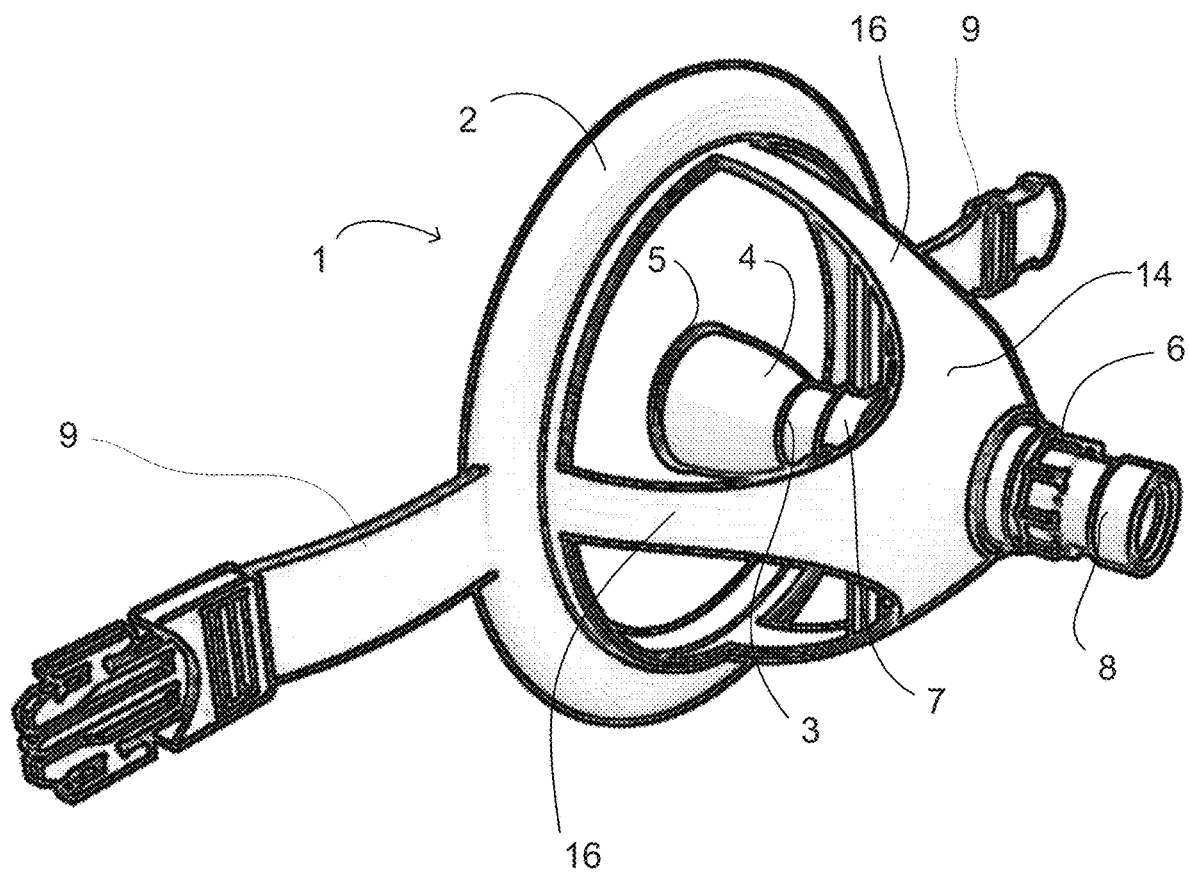

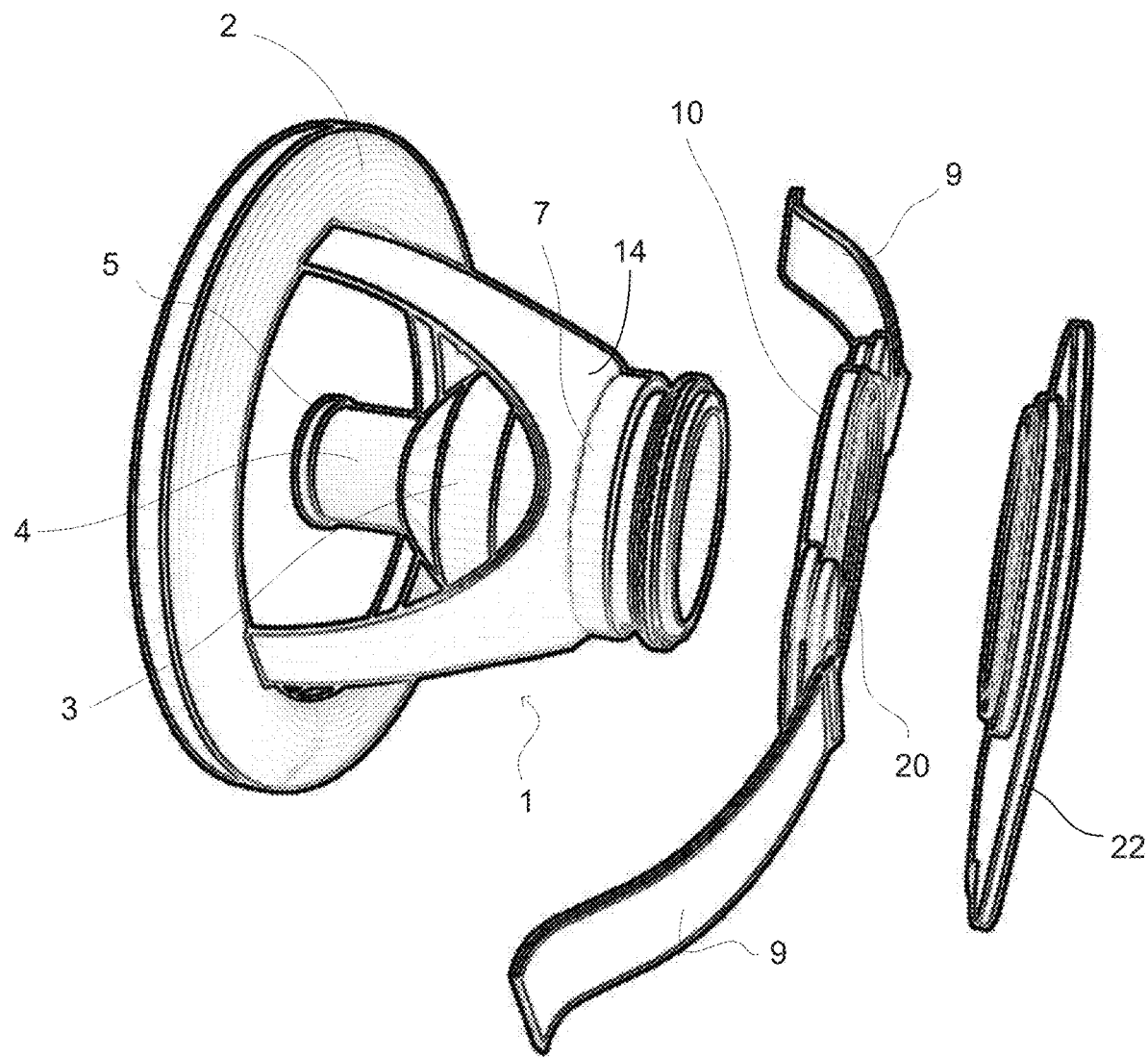
- Fig. 5 -

- Fig. 6 -
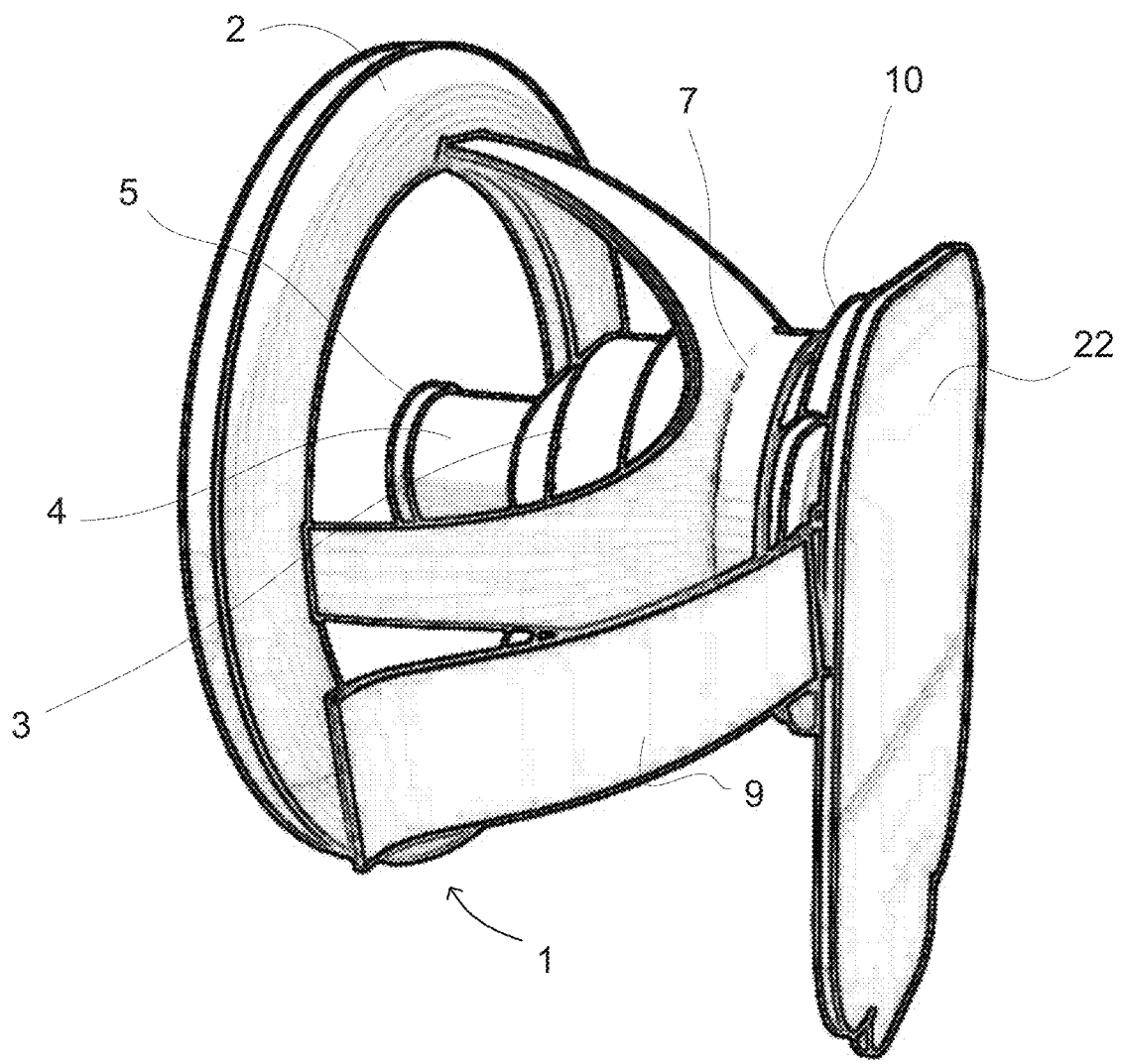

- Fig. 7 -
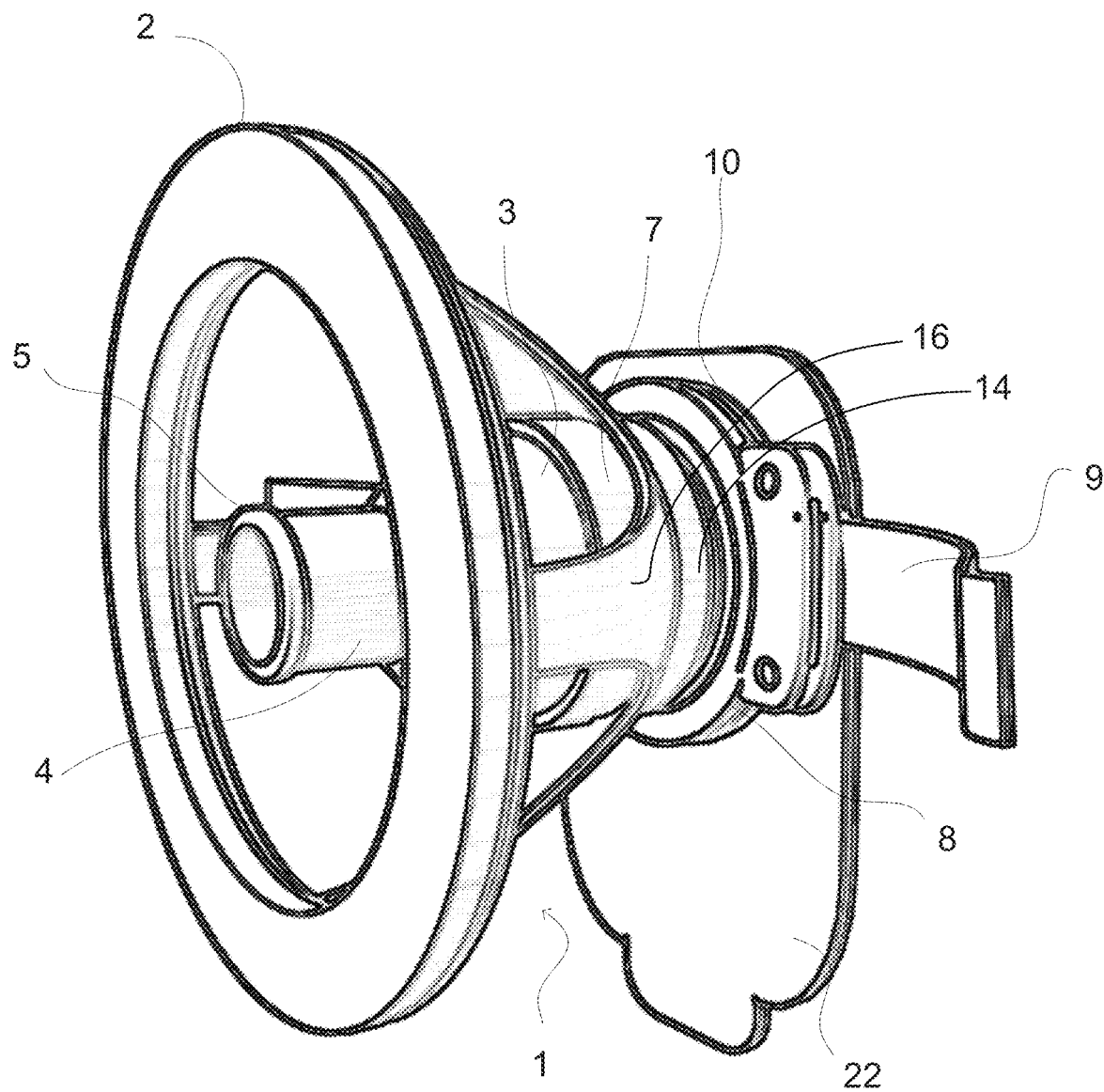

- Fig. 8 -
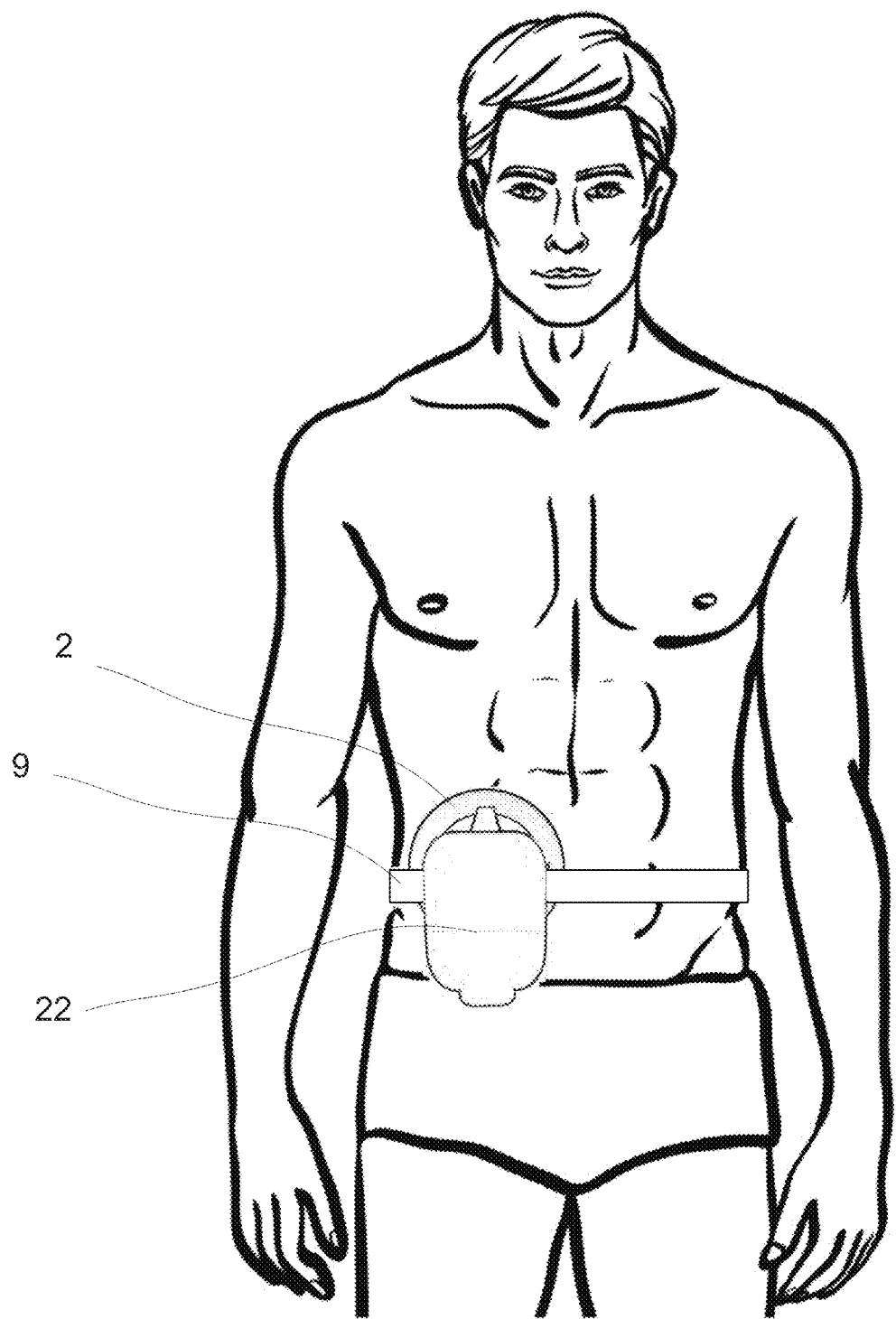

- Fig. 9 -
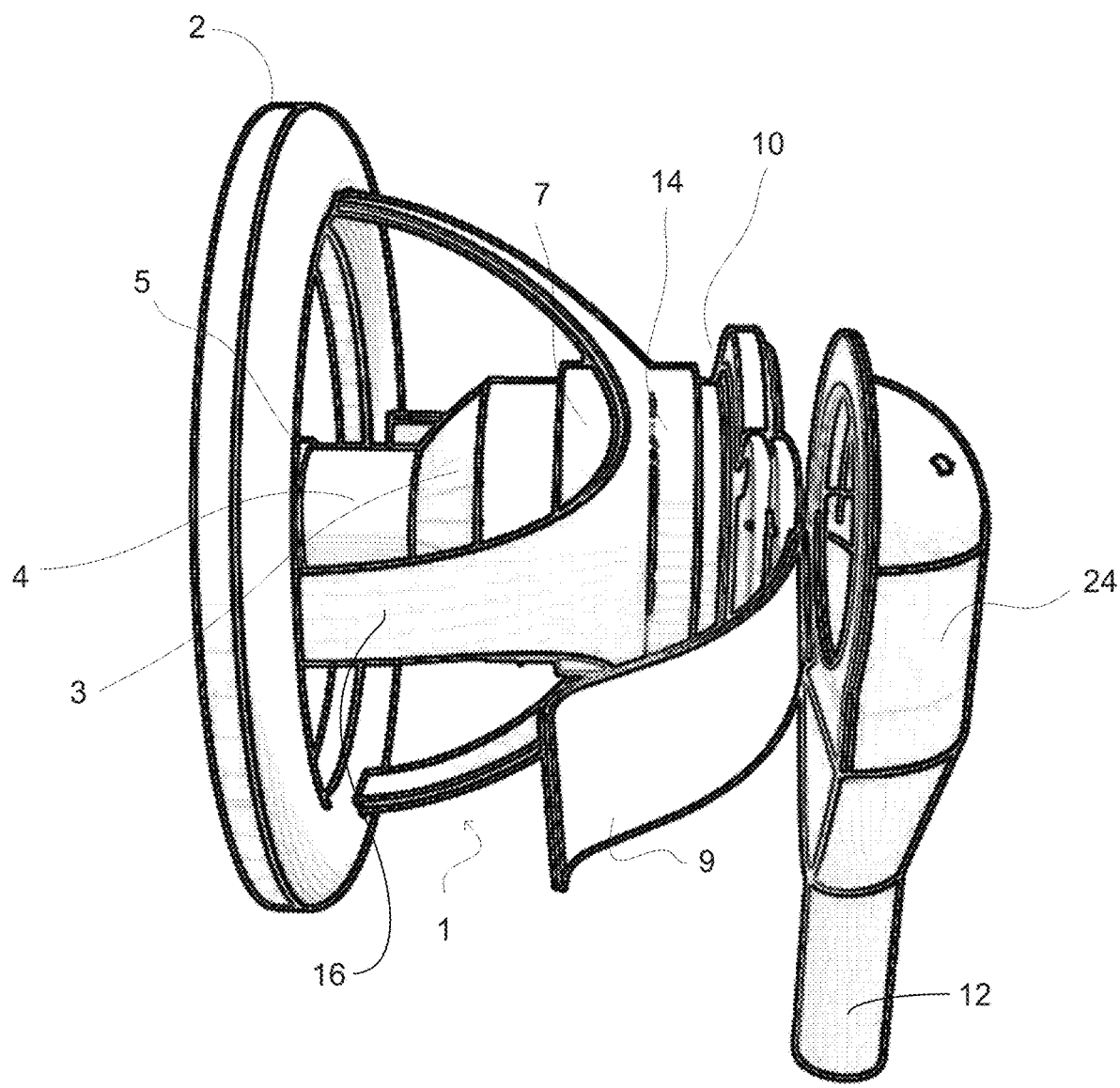

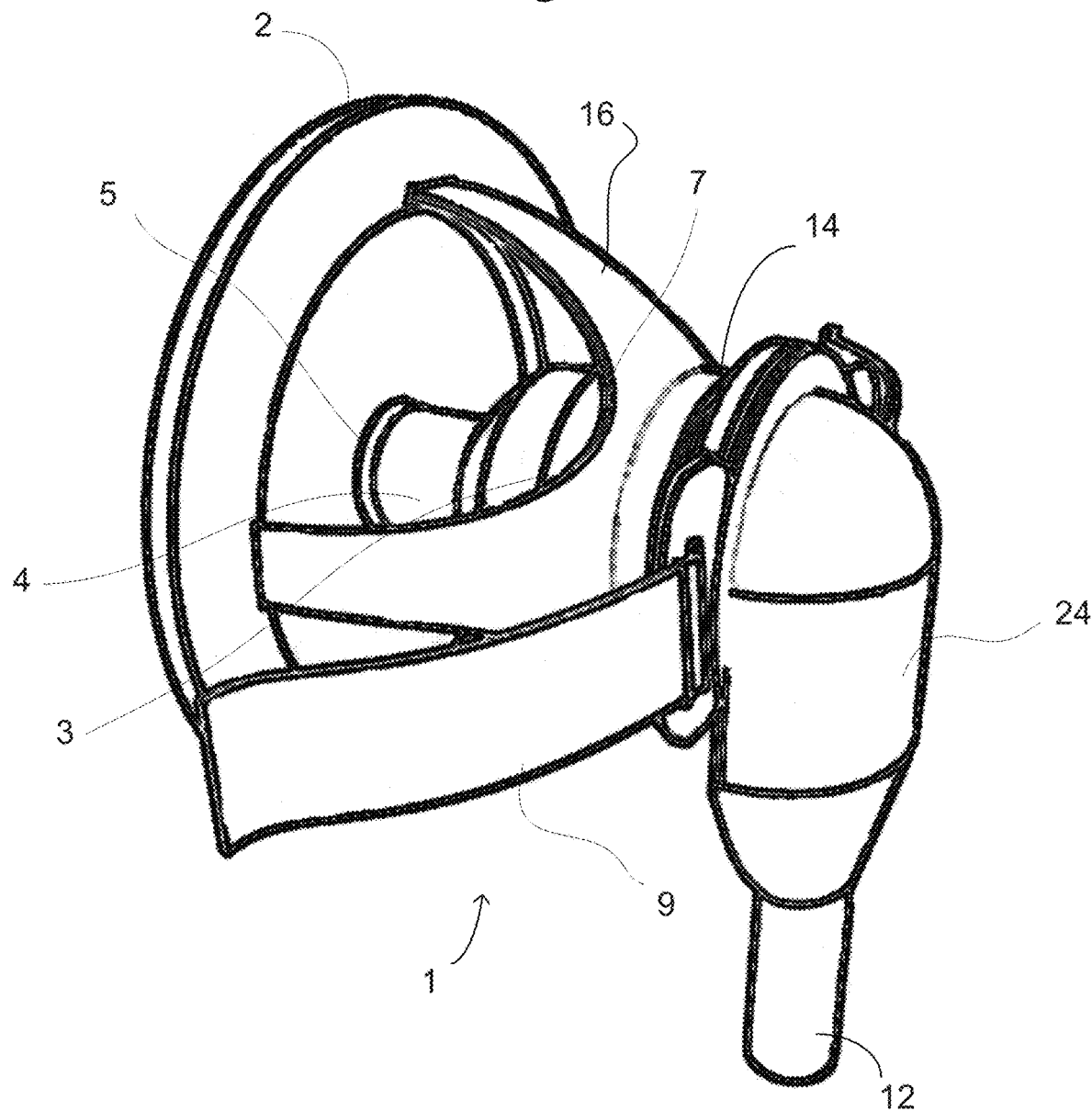
- Fig. 10 -

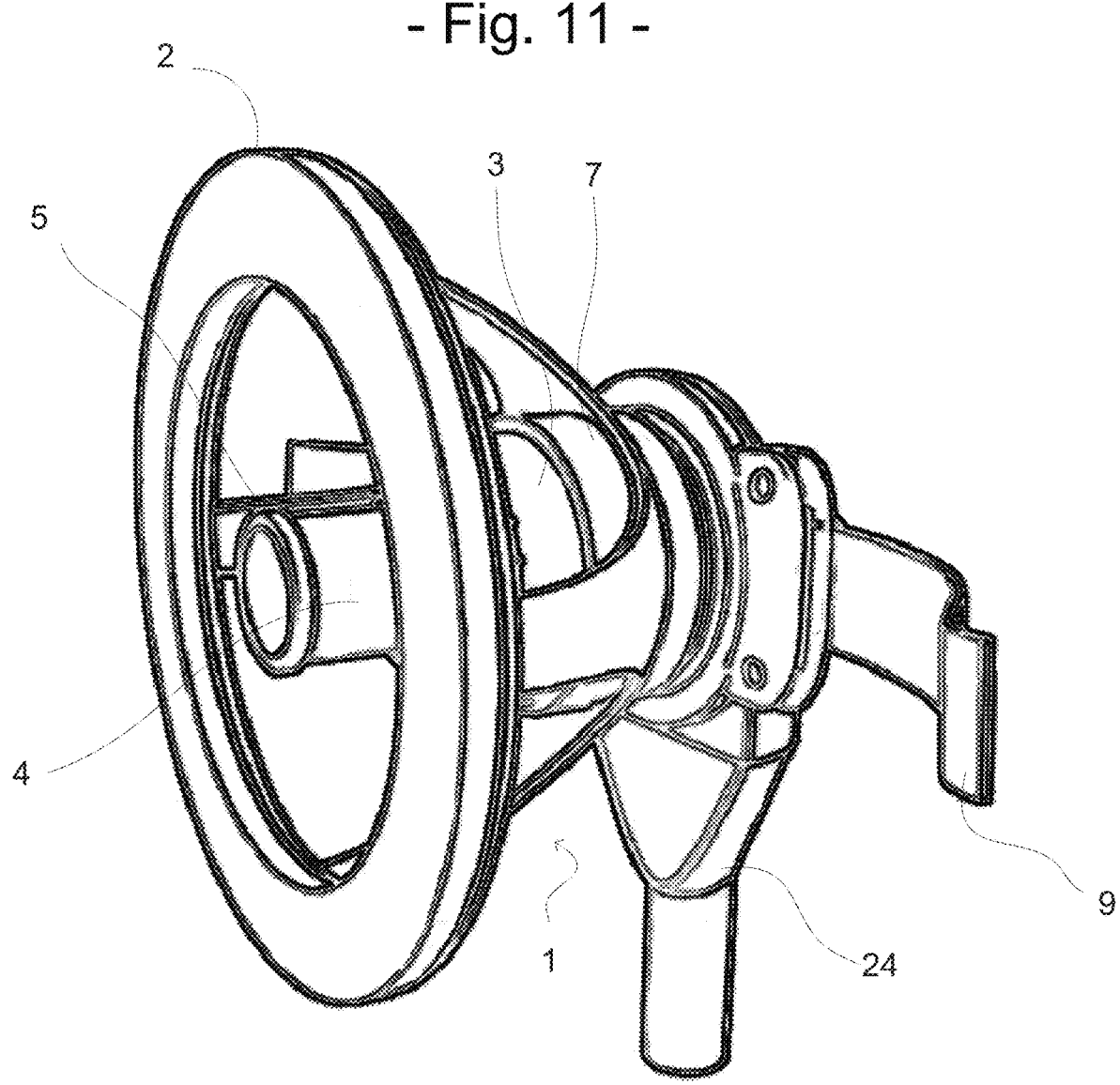
- Fig. 11 -

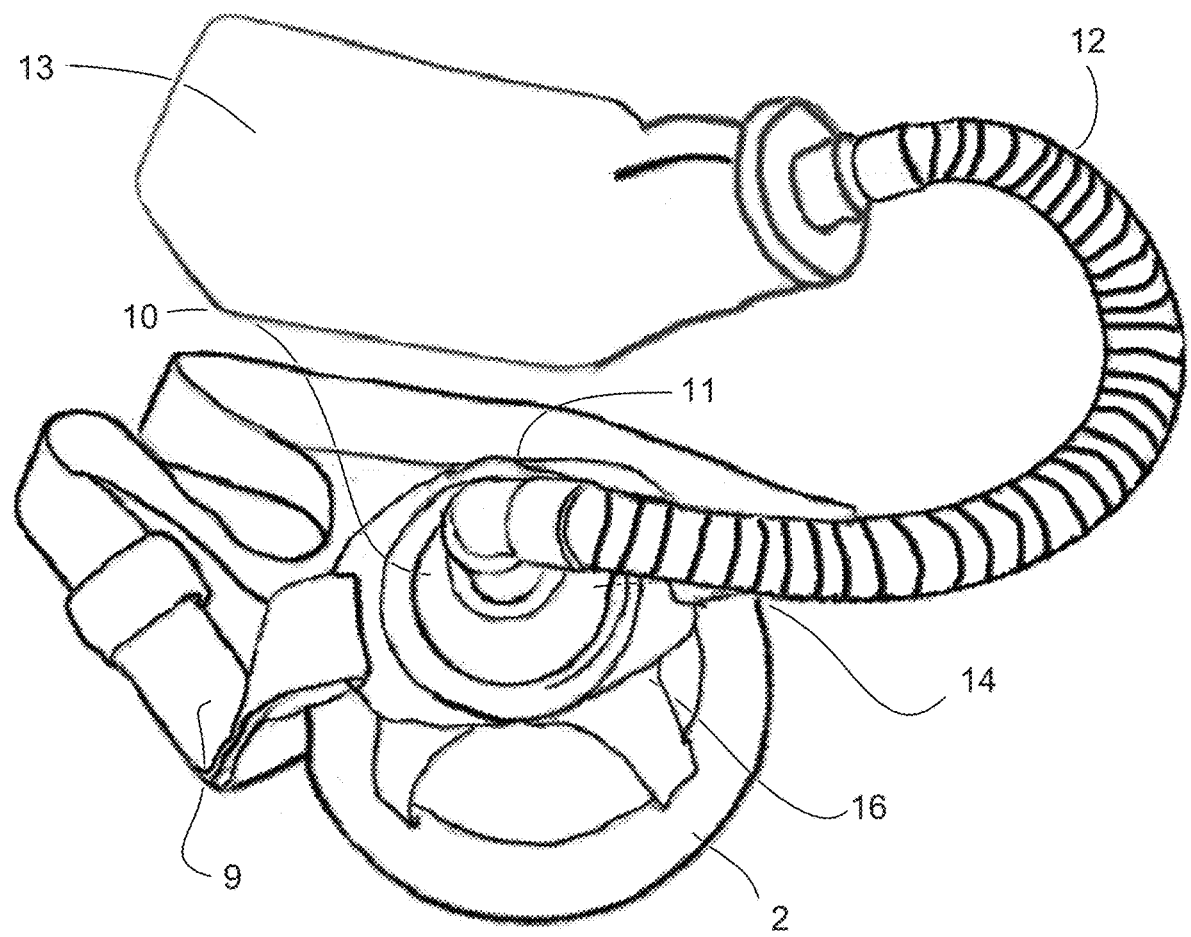
- Fig. 12 -

- Fig. 13 -
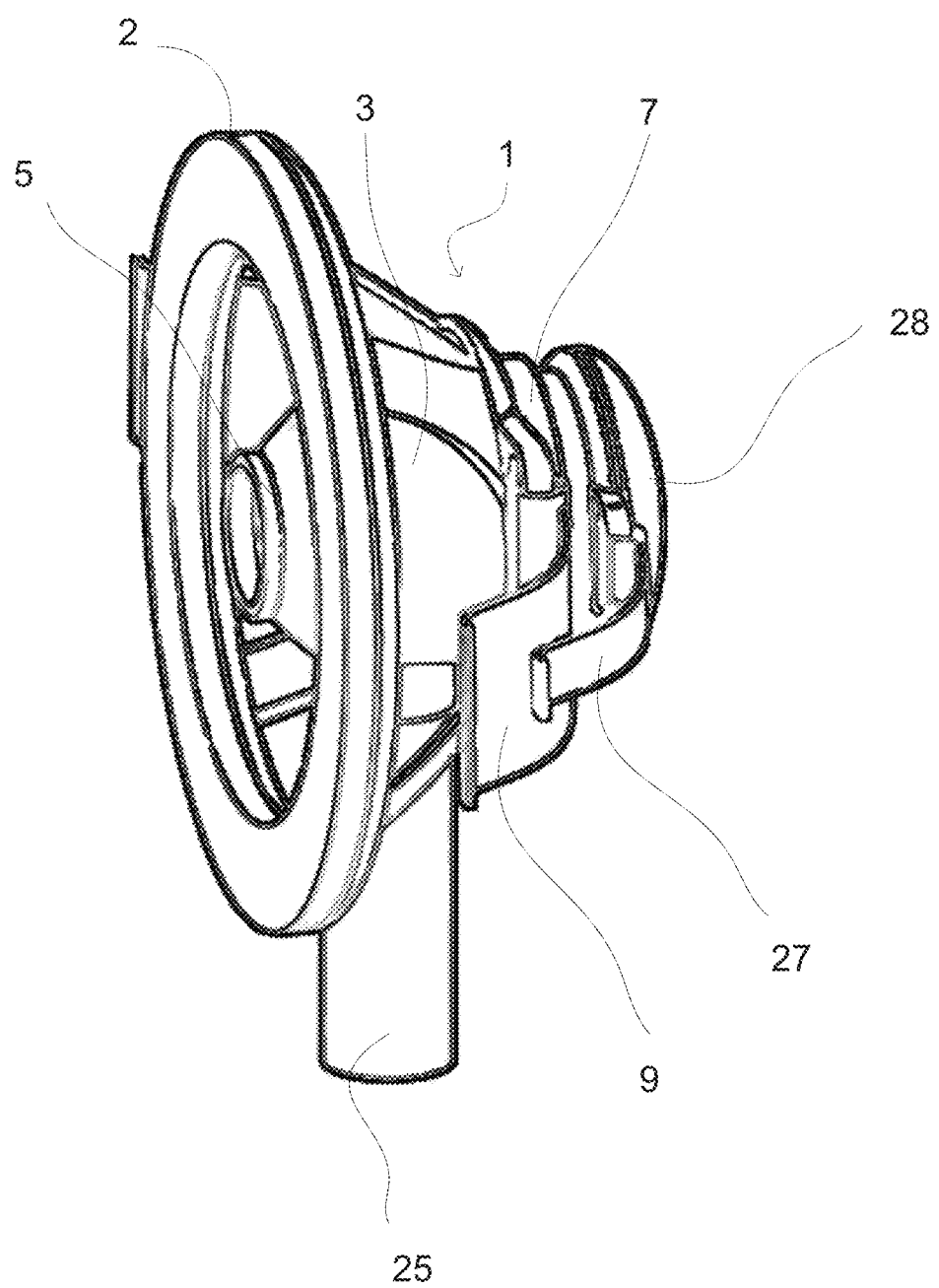

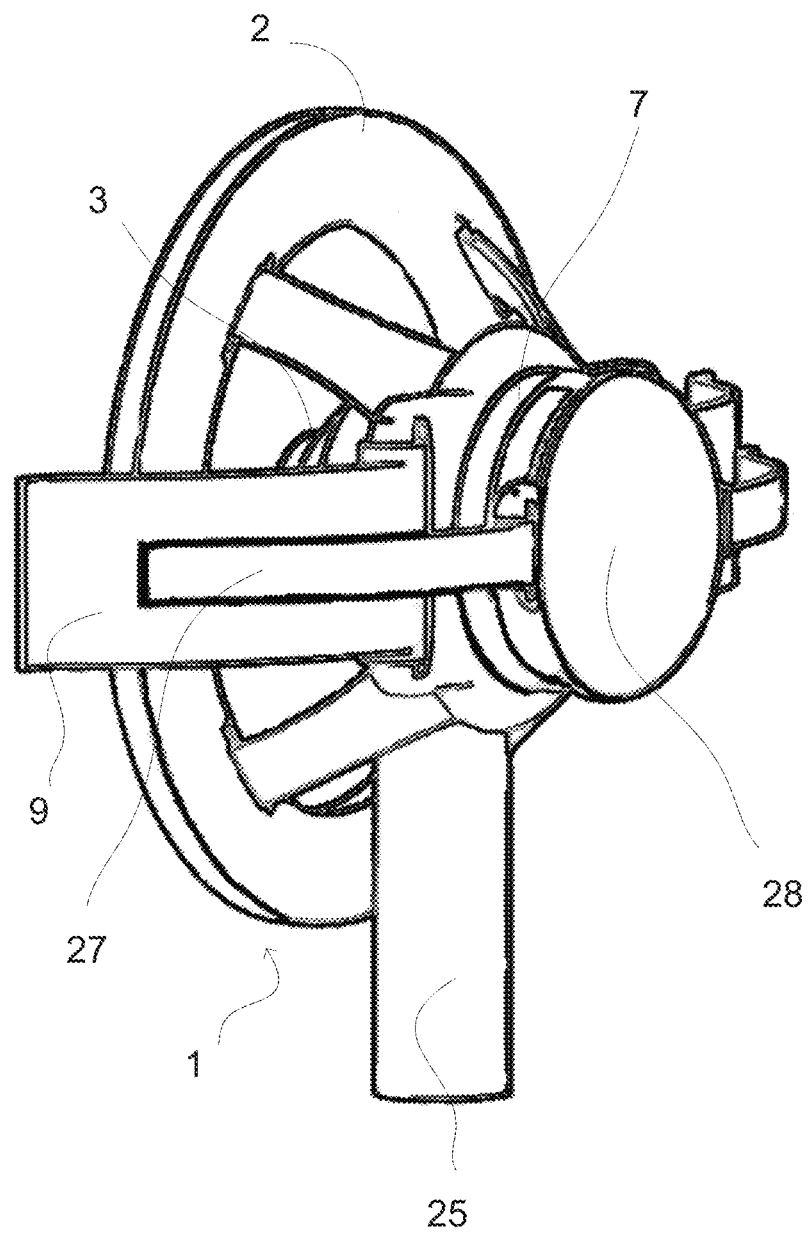
- Fig. 14 -

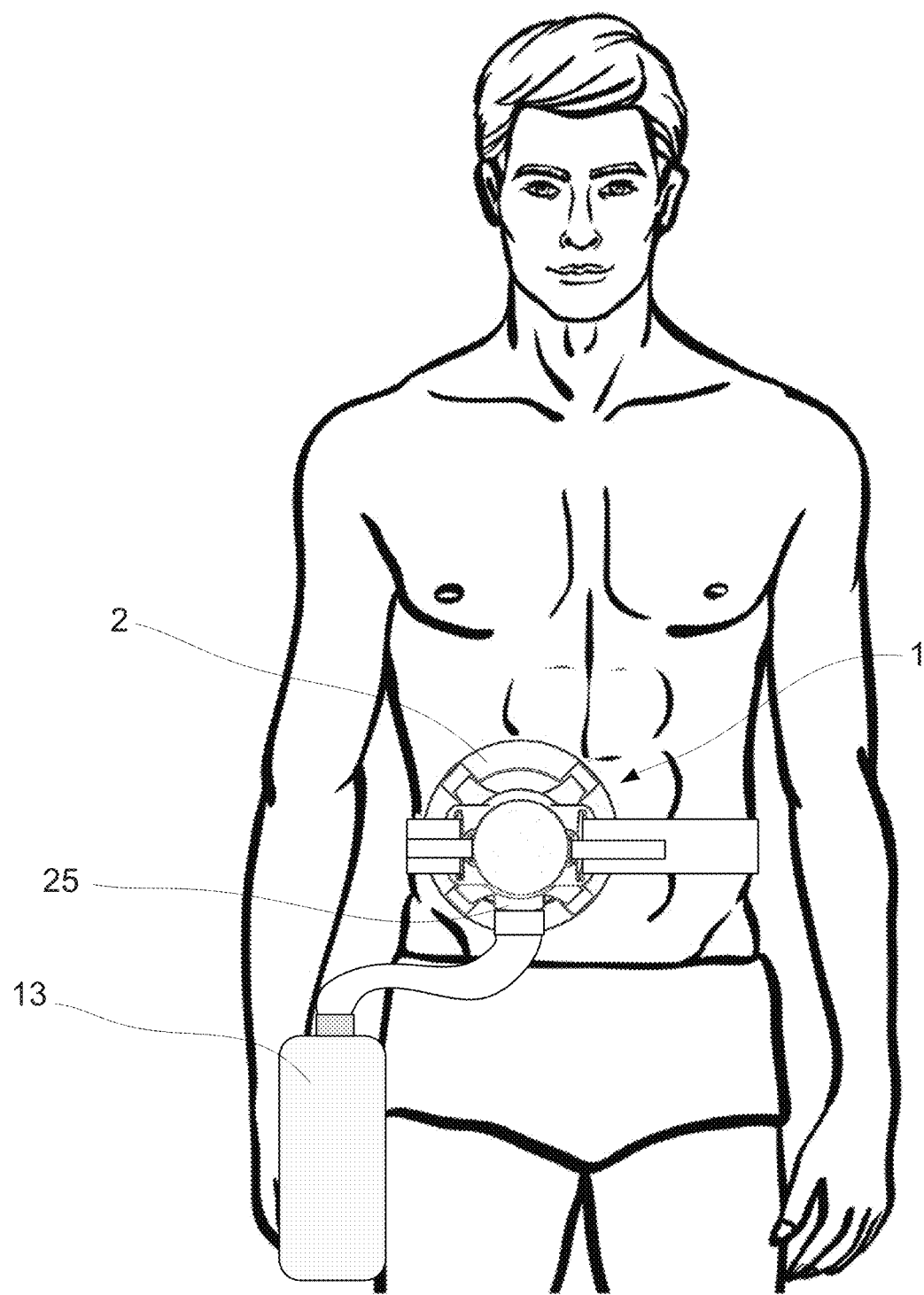
- Fig. 15 -

- Fig. 16 -
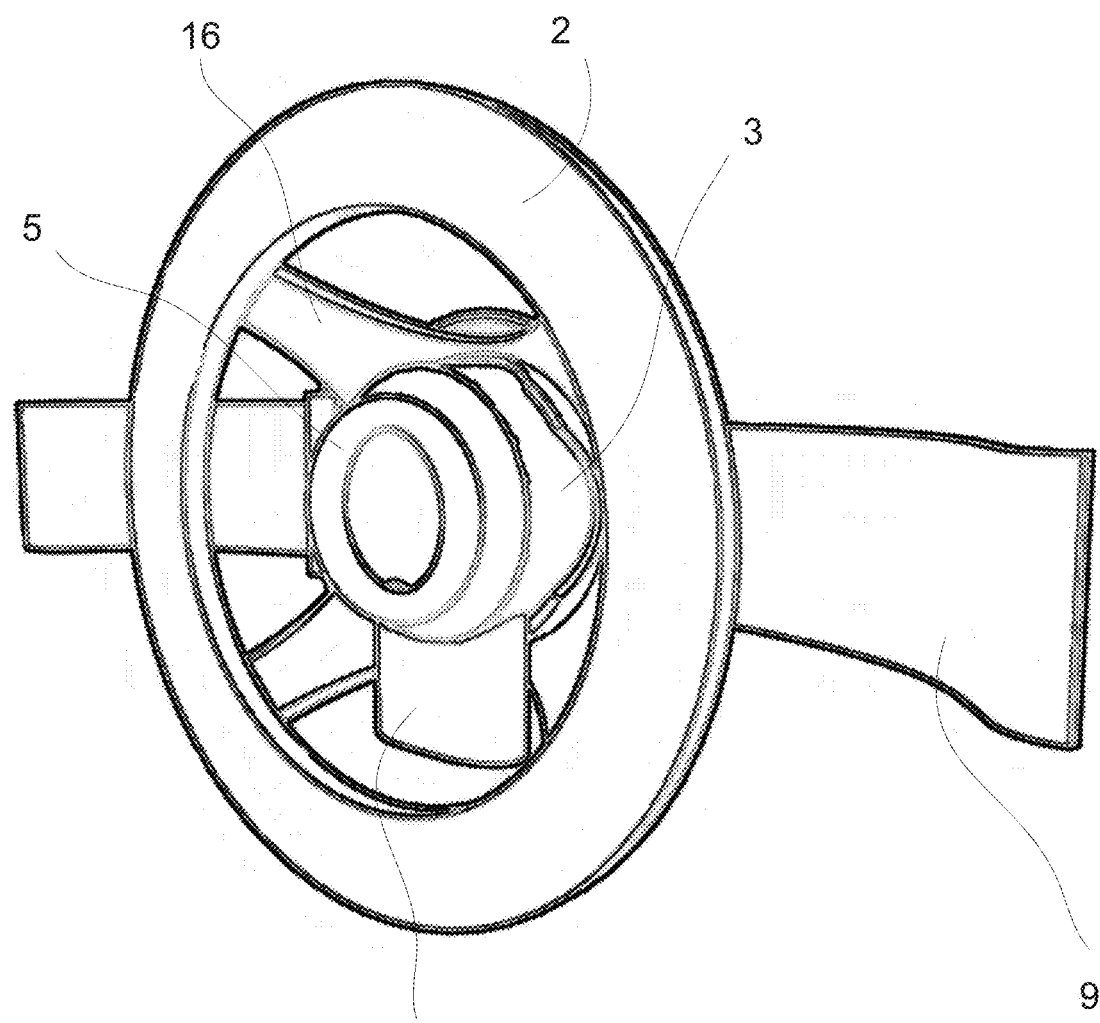

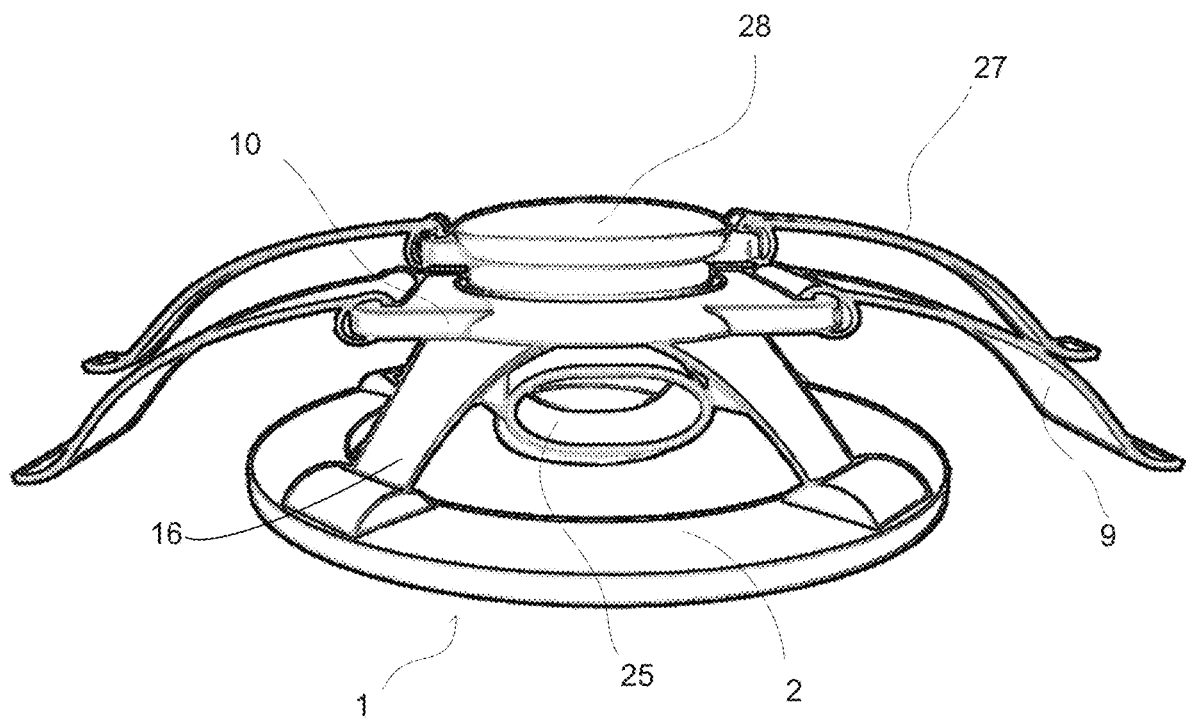
- Fig. 17 -

- Fig. 18 -
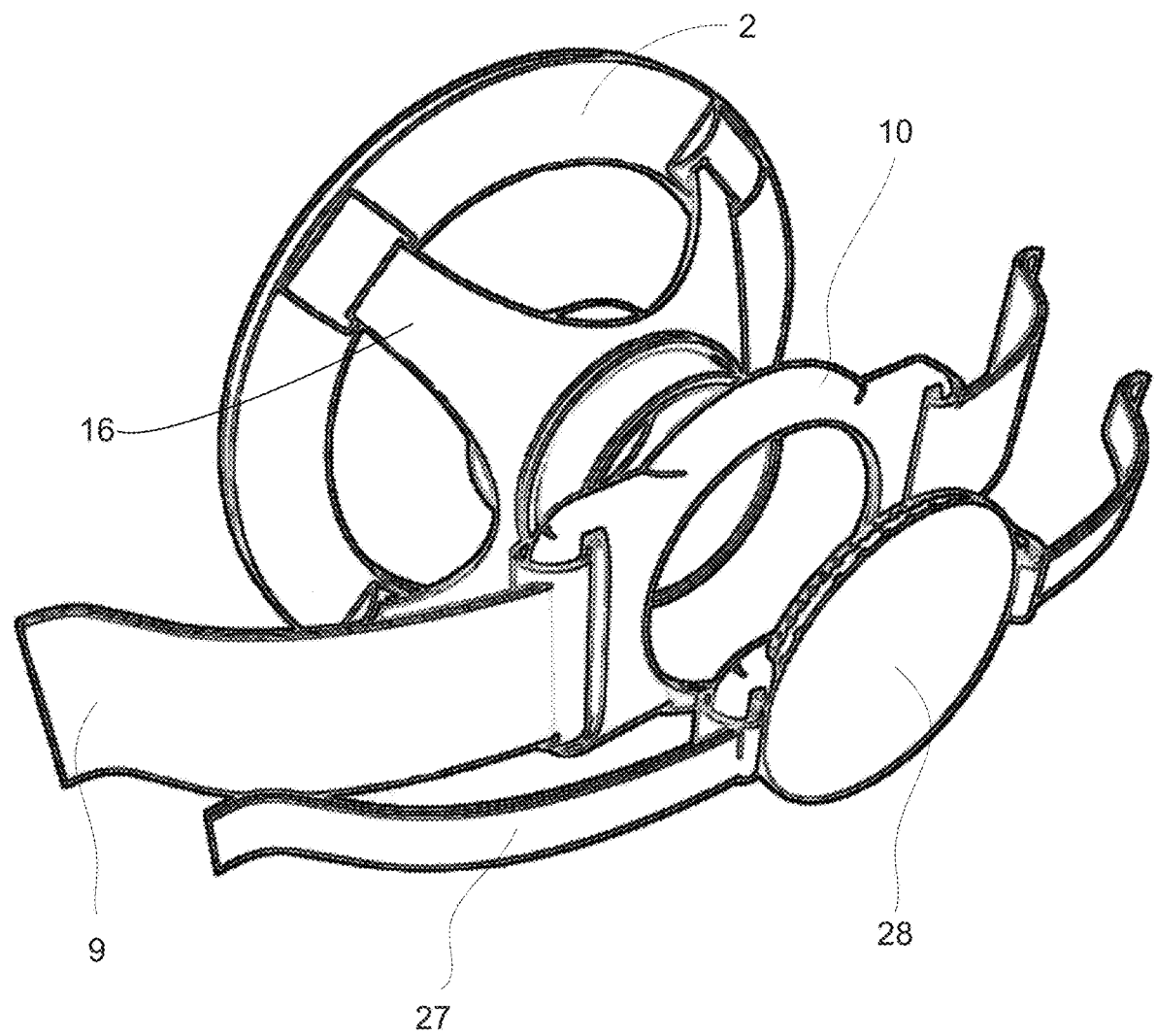

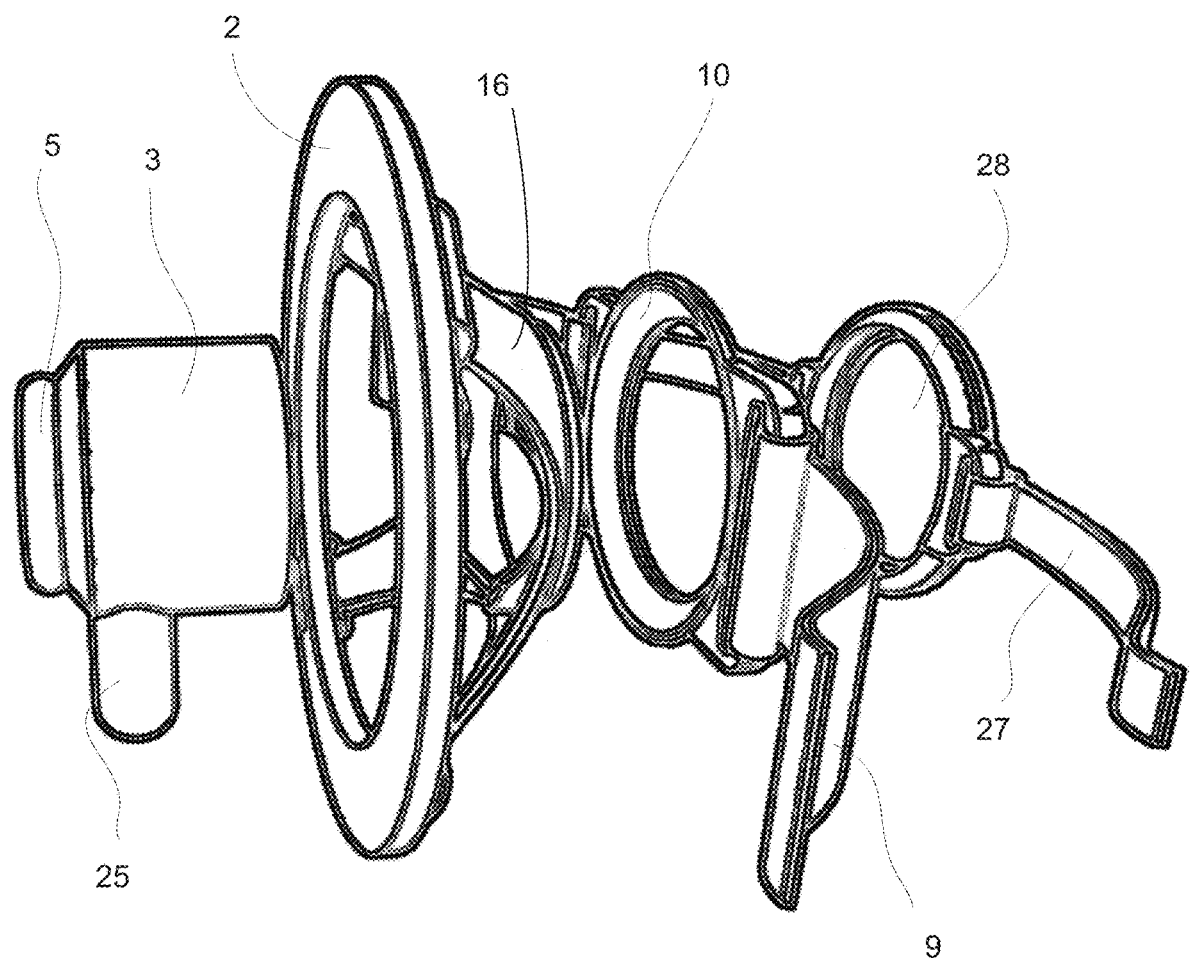
- Fig. 19 -

- Fig. 20 -
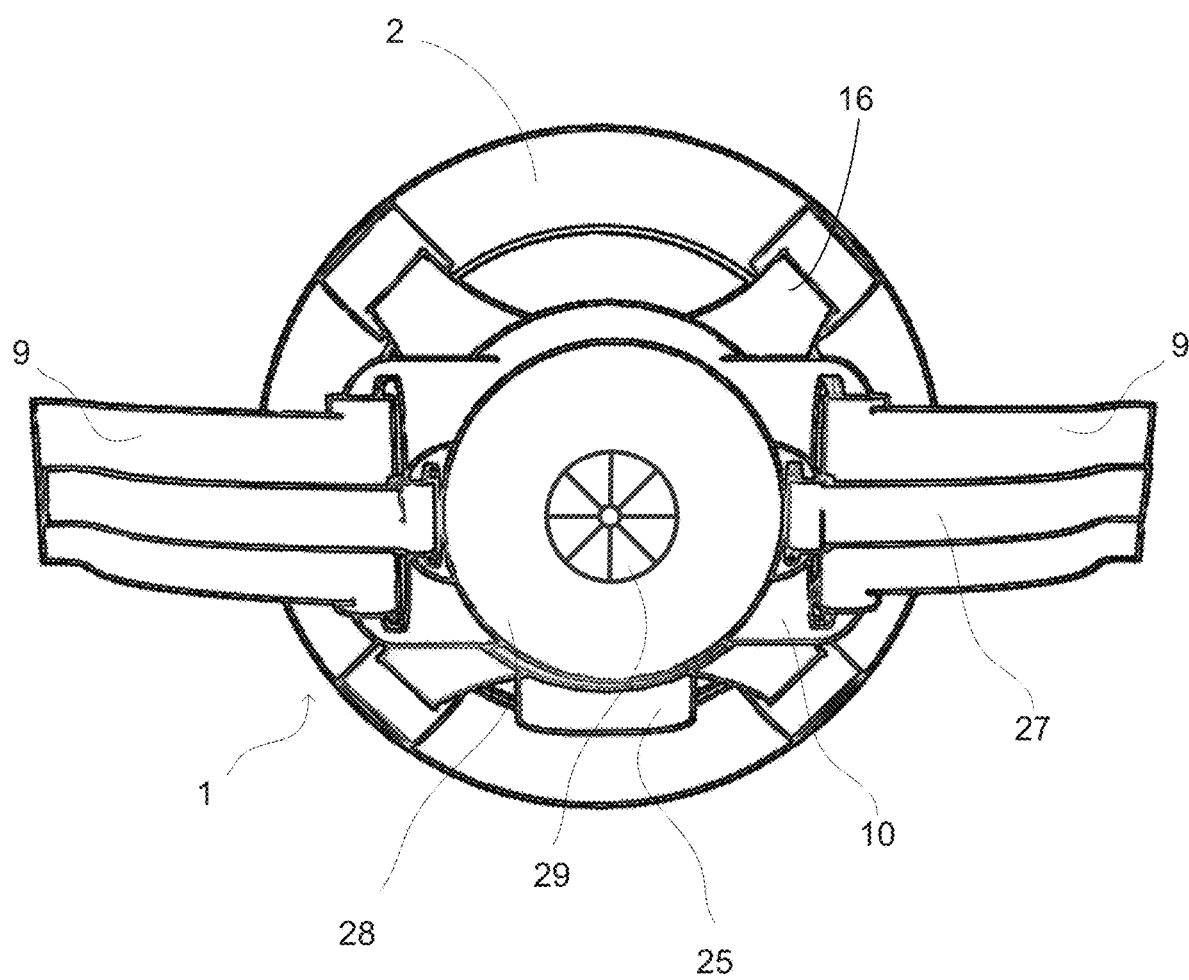

OSTOMY OUTPUT DIVERSION DEVICE

CROSS REFERENCE TO RELATED APPLICATIONS

The present application is a continuation-in-part of U.S. Ser. No. 16/679,960 entitled Ostomy Output Diversion Device filed on Nov. 11, 2019, which is a continuation-in-part of U.S. Ser. No. 16/518,506 entitled Ostomy Output Diversion Device filed on Jul. 22, 2019. All of the foregoing applications are hereby incorporated by reference in their entireties.

FIELD OF THE INVENTION

The present invention relates to a medical device designed to capture ostomy effluent output without the need of an adhesive-based ostomy pouching system, allowing extended periods of time without skin being covered, and designed to improve chronic peristomal skin conditions.

BACKGROUND OF THE INVENTION

Surgical procedures such as a colostomy, urostomy and ileostomy involve rerouting of the colon or ureter so that effluent can be discharged through an artificial opening formed in the ostomy patient's (also referred to herein as ostomate) body. This artificial opening, called a stoma, is typically located in the abdomen and may be about 0.5 to 2.5 inches or more in diameter.

The new artificial opening, or stoma, made on the abdominal wall, has no voluntary sphincter control by the ostomate. Collection of involuntary waste seepage is by a pouching system, typically comprising a pouch and baseplate, or other receptacle attached to the ostomate's body, where the pouching system is disposed of after use, and replaced with a fresh pouching system. Typically, such pouching systems are attached to the body over the stoma by means of a baseplate with adhesive backing which must be positioned over the stoma with precision to achieve a reliable attachment and seal. It is essential that this baseplate be mounted directly and concentrically over the stoma and further, that it be tightly secured to the body, otherwise leakage of waste onto the surrounding skin area can occur.

The pouching system is typically replaced every 2 to 5 days, with the replacement process typically taking 15 to 30 minutes. During the pouching system replacement process, while the pouching system is removed and the peristomal skin is exposed, the common practice has been to first clean and dry the peristomal skin, then treat and medicate any skin irregularities, followed by thorough drying of the skin and application of the new pouching system. Continued seepage of effluent and other uncontrollable factors, often cause the ostomate to hasten the process and apply the new pouching system prematurely, leading to further exacerbation of any emerging or existing skin conditions. Patients often experience acute or chronic peristomal skin conditions caused by medical adhesive related skin injury, moisture associated skin damage, allergic reactions to ostomy supply materials, and extended wear times with limited time to adequately treat skin before applying the new pouching system.

Attempts have been made to improve the procedures mentioned above for replacing pouches and cleaning a stoma or fistula and surrounding areas. The following references represent some of these past attempts, and each of the documents cited below are hereby expressly incorporated herein by reference, in their entireties:

WIPO Patent Publication Number WO2001000260 Colostomy Pump Device

A device (10) for evacuating waste product through an orifice in a mammalian body, the device (10) including a chamber (11) having an irrigating means (16) for introducing an irrigating fluid into the orifice and a suction means (40) for removing the irrigating fluid and waste products from the orifice.

U.S. Application No. 20130180294 Ostomy Device, Apparatus and System

Devices for insertion into a stoma formed in a patient's body are provided, comprising a tube having distal and proximal ends and defining a path for movement of waste. To retain the device in the stoma and seal the stoma, the tube includes a retention mechanism located on the distal end and/or a sealing mechanism extending along a length of the tube between the proximal and distal ends. Collection apparatus for collecting waste from a patient's body also are provided, comprising a waste pouch and a connector for connecting the collection apparatus to a device inserted into a stoma. Additionally, waste collection systems for collecting waste from a patient's body are provided, comprising a tube for insertion into a stoma and a waste pouch. Each system may comprise a separate tube and waste pouch or the tube and waste pouch may be formed as an integral, inseparable component.

Canadian Patent No. CN1074687406 Stoma Drainage Bag Support Frame

The invention provides a stoma drainage bag support frame. The support frame comprises a first annular bracket, a second annular bracket and connecting rods, the outer diameter of the second annular bracket is smaller than the inner diameter of an opening of a drainage bag, the number of the connecting rods is three, the connecting rods are evenly arranged on the first annular bracket and the second annular bracket and connect the first annular bracket with the second annular bracket, the vertical distance between the first annular bracket and the second annular bracket is 2-5 cm, and the second annular bracket is provided with three convex portions, wherein the three convex portions are arranged at the joints of the connecting rods and the second annular bracket, externally protrude in a same plane with the second annular bracket and are used for fixing the bracket in a base plate ring of the stoma drainage bag. The stoma drainage bag support frame is placed between a drainage base plate and the drainage bag, by means of the support frame, damage to or necroses of a gut or an external segment of a ureter under pressure caused by negative pressure generated by drainage is avoided, and meanwhile, the phenomenon of liquid backflow caused by negative pressure effect and infection of a patient are avoided, so that health of the patient is guaranteed.

Each of the devices and methods set forth above are useful, but these advancements also have disadvantages. It would be desirable, therefore, to provide an ostomy output diversion device that is simple to use, inexpensive to manufacture, and which provides a useful and efficient way to maintain the health and cleanliness of a patient's stoma and surrounding skin and tissue.

BRIEF SUMMARY OF THE INVENTION

The present invention relates to a medical device designed to capture ostomy effluent output without the need of an ostomy pouching system, allowing extended periods of time without skin being covered by an adhesive baseplate, and designed to improve chronic and acute peristomal skin conditions.

In a first embodiment, the ostomy output diversion device includes a main body member, the outer frame of the main body member is shaped in a manner to extend away from the body, with space between the frame supports to allow open access to the peristomal skin, allowing patients to treat and medicate the peristomal skin, and to leave the skin uncovered for an extended period of time, an inner tube guide for aligning and supporting an inner tube, an inner tube member positioned through the center of the main body member and inner tube guide and adjustable to allow movement within the main body member and inner tube guide, a stoma-sized adapter attached to the bottom end of the inner tube member and sized to fit over the stoma, a sealing ring attached to the bottom of the stoma-sized adapter to prevent effluent from seeping between the adapter and adjacent skin, a pressure adjustment lock to apply adequate pressure between the stoma-sized adapter and the adjacent skin during application, an effluent draining tube attached to the drain tube connector on the distal end of the inner tube, the opposite end of the effluent draining tube leading to a reservoir container to contain effluent output, with an adjustable body support strap used to secure the device to the body during application.

DESCRIPTION OF THE DRAWINGS

These and other features, aspects, and advantages of the present invention will become better understood with regard to the following description and accompanying drawings where:

FIG. 1 is a perspective view of one embodiment of an ostomy output diversion device, including a main body member, attached to a base ring, and having an inner tube member positioned through the center of the main body member, inner tube guide, and a stoma-sized adapter, with a sealing ring attached, and an adjustable body support strap used to secure the device to the body;

FIG. 2 is a perspective view to illustrate one embodiment of the ostomy output diversion device strapped on a person in a typical manner, and a drain tube attached to a reservoir;

FIG. 3A is a perspective view of one embodiment of the ostomy output diversion device, and the removable strap and ring positioned on the device;

FIG. 3B is a perspective, exploded view of one embodiment of the ostomy output diversion device, wherein the strap ring and strap are removed from the outer frame;

FIG. 4 is a perspective view of one embodiment of an ostomy output diversion device showing a body support strap used to secure the ostomy output diversion device to the body;

FIG. 5 is a perspective, exploded view of one embodiment of an ostomy output diversion device, wherein the strap ring and strap are removed from the outer frame, and further showing a pouch mounting ring on a distal portion of the strap ring for connection with an ostomy pouch;

FIG. 6 is a perspective view of the embodiment of an ostomy output diversion device shown in FIG. 5, wherein the strap ring is secured over the outer frame, and the ostomy pouch is connected to the pouch mounting ring;

FIG. 7 is a perspective view of the embodiment of an ostomy output diversion device shown in FIG. 5, wherein the strap ring is secured over the outer frame, and the ostomy pouch is connected to the pouch mounting ring;

FIG. 8 is a perspective view of the embodiment of an ostomy output diversion device shown in FIG. 5, wherein the strap ring is secured over the outer frame, and the ostomy pouch is connected to the pouch mounting ring, and wherein the apparatus is strapped onto a patient's body;

FIG. 9 is a perspective, exploded view of one embodiment of an ostomy output diversion device, wherein the strap ring is removably secured over the outer frame, and wherein an output adapter is attachable to the strap ring;

FIG. 10 is a perspective view of one embodiment of an ostomy output diversion device, wherein the strap ring is removably secured over the outer frame, and wherein an output adapter is removably attached to the strap ring;

FIG. 11 is a perspective view of one embodiment of an ostomy output diversion device, wherein the strap ring is removably secured over the outer frame, and wherein an output adapter is removably attached to the strap ring;

FIG. 12 is a perspective view of one embodiment of an ostomy output diversion device, including a main body member attached to a base ring, and having an inner tube member positioned through the center of the main body member, inner tube guide, and a stoma-sized adapter with a sealing ring attached thereto, and an adjustable body support strap used to secure the device to the body, and further including an elbow member attached to a drain tube connector, and a drainage tube extending between the elbow member and a reservoir for receiving effluent;

FIG. 13 is a perspective view of another embodiment of an ostomy output diversion device, including a main body member attached to a base ring, and having an inner tube connected to the main body member, wherein the inner tribe includes a first opening for placement over a stoma or fistula, and a second opening for attachment to a drainage channel that may be operatively connected to a reservoir; and FIG. 14 is a perspective view of the ostomy output diversion device shown in FIG. 13.

FIG. 15 is a perspective view of the embodiment of an ostomy output diversion device shown in FIG. 13, wherein the strap ring is secured to the outer frame, and wherein the apparatus is strapped onto a patient's body;

FIG. 16 is a perspective view of the ostomy output diversion device shown in FIG. 13;

FIG. 17 is a perspective view of the ostomy output diversion device shown in FIG. 13;

FIG. 18 is a perspective, exploded view of one embodiment of an ostomy output diversion device, wherein the strap ring and strap are removed from the outer frame, and further showing a concealing cap and tension straps;

FIG. 19 is a perspective, exploded view of one embodiment of an ostomy output diversion device, wherein the inner tube and drainage adapter are separated from the outer frame, and further showing the strap ring and strap removed from the outer frame, and further showing a concealing cap and tension straps;

FIG. 20 is a perspective view of one embodiment of an ostomy output device showing an odor filter integral to the concealing cap;

DETAILED DESCRIPTION OF THE INVENTION

Figure 21:
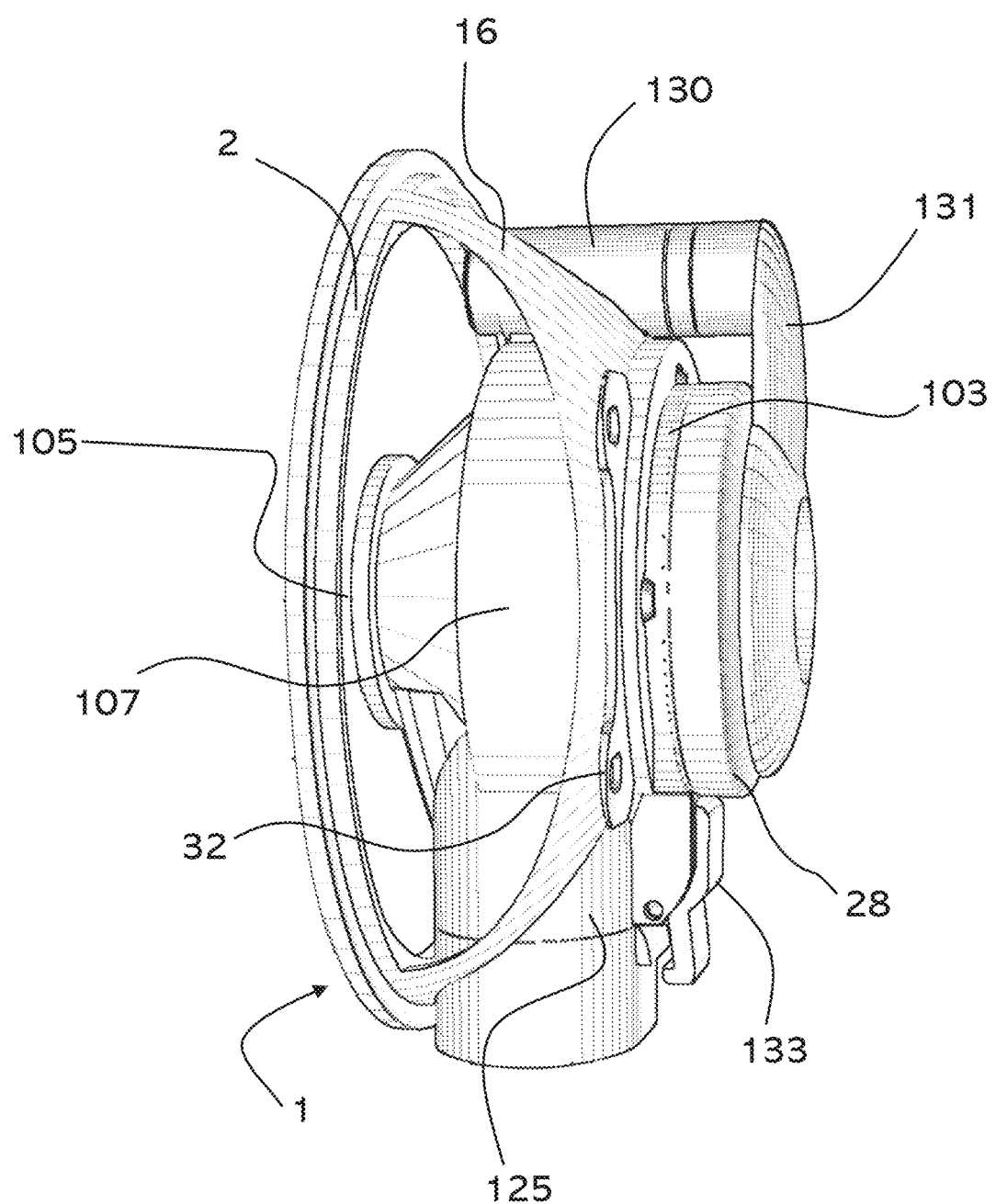
FIG. 21 is a perspective view of another embodiment of an ostomy output device, showing a base ring attached to an outer frame member including a cylinder guide that is movably attached to a diverter cylinder having a vertical output channel at a bottom thereof and a concealing cap with a spring loaded tension spring rod in a retracted position.
Figure 22:
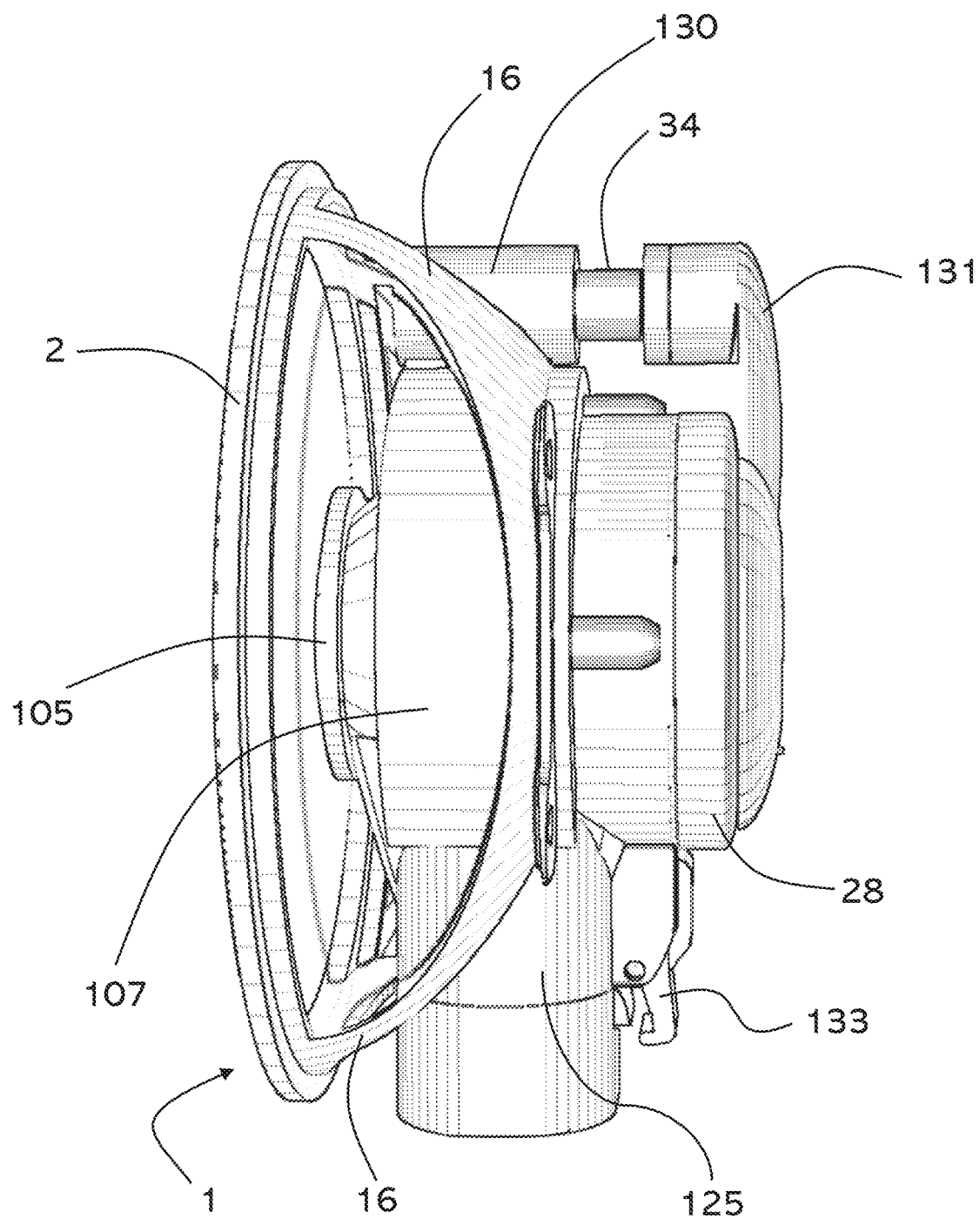
FIG. 22 is a perspective view of the embodiment of the ostomy output device shown in FIG. 21, wherein the spring-loaded tension spring rod is shown in an extended position.
Figure 23:
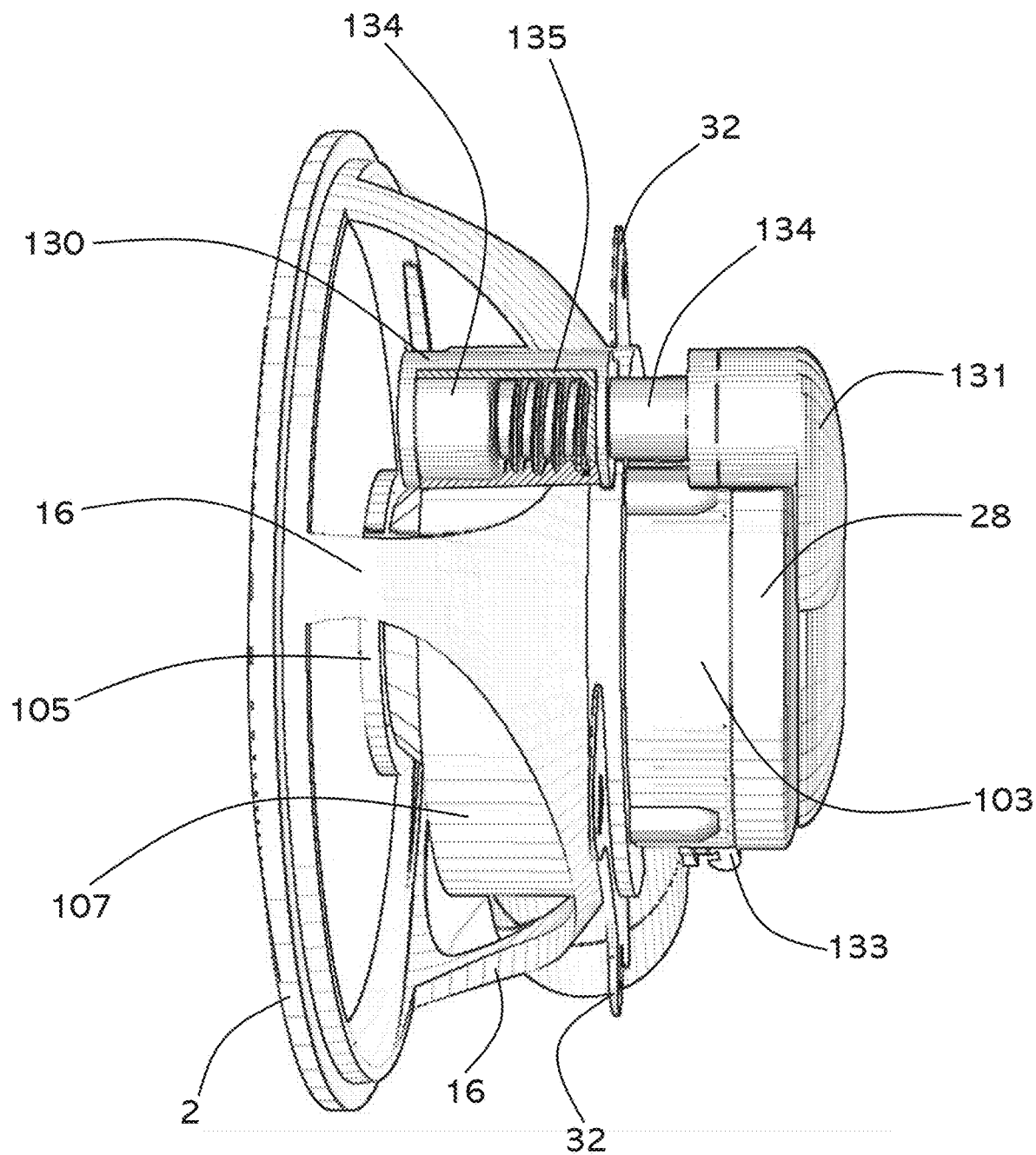
FIG. 23 is a perspective view of the embodiment of the ostomy output device shown in FIG. 21, including a cutaway view of the tension spring housing showing the spring-loaded tension spring rod disposed therein.

FIG. 1 illustrates an embodiment of the present invention whereby the ostomy output diversion device includes a main body member 1 having a base ring 2, support members 16 attached to the base ring 2 on a first end thereof, and an outer frame 14 attached to the support members 16 on a second end thereof. In a preferred embodiment, the outer frame 14 extends away from the patient's body, with space provided between support members 16 to allow open access to the peristomal skin. The base ring 2 may be constructed of any suitable material, but preferably of soft material for skin contact comfort. In one embodiment, the base ring 2 may be malleable, so that a patient may form the base ring 2 into any desired shape or configuration to conform to the contour of his or her abdominal shape, as desired, for ease of use. In this embodiment, the base ring 2 may be made from flexible materials, such as rubber, foam, or other suitable formable materials, and may also include a structural wire to allow the base ring to maintain the desired configuration formed by the patient. In some embodiments, the base ring 2 may be removable and replaceable with base rings of other sizes, shapes, or configurations.

In a preferred embodiment, the ostomy diversion device further includes a centrally located inner tube member 3, positioned through the center of the main body member 1 and an inner tube guide 7 that is held in place by support spokes 15 that are attached to the inner portion of the support members 16. A stoma-sized adapter 4 is attached to the proximal end of the inner tube member 3 and sized to fit over the stoma or fistula, and the adapter 4 includes a sealing ring 5 that is used to prevent effluent from seeping between the stoma-sized adapter 4 and adjacent skin. The inner tube member 3 is preferably telescopic in nature, and is incrementally or infinitely adjustable inwardly and outwardly in linear fashion, in order to allow movement within the main body member 1. A pressure adjustment lock 6 is used to apply and maintain adequate pressure between the stomia-sized adapter 4 and the adjacent skin during application. In use, when the base ring is placed in the proper position against a patient's skin, the inner tube member 3 may be extended toward the stoma or fistula to ensure a tight fit, and the pressure adjustment lock 6 is used to maintain the extended position thereof. The pressure adjustment lock 6 may be disengaged and repositioned during use, or after use, as desired.

In a preferred embodiment, the ostomy output diversion device includes a removable body support strap 9 and strap mounting ring 10, used to secure the ostomy output diversion device to the body during application. The removable body support strap 9 may be affixed to the strap mounting ring 10, which fits over or onto the distal portion of the outer frame member 14, as shown in FIGS. 3A and 3B, or the strap 9 may be affixed to other portions of the device, such as the base ring 2 as shown in FIG. 4. Any suitable strap means may be used to attach the device to a patient's body, so long as the device, and specifically the sealing ring 5 of the stoma-sized adapter 4 are held firmly in place against the patient's skin, in order to prevent any effluent from leaking therefrom.

In a preferred embodiment, the ostomy output diversion device includes a drain tube connector 8, used to connect a drain tube 12 to the distal end of the inner tube 3, and to a reservoir 13 to collect ostomy output. Essentially, a clear drainage passage is formed from the adapter 4 through the inner tube 3, the tube connector 8, and into the drain tube 12, so that effluent may pass unobstructed from the stoma or fistula to the reservoir 13 without leakage from any point along the way. In a preferred embodiment, a hollow elbow joint 11 may be affixed to the tube connector 8 on a first side thereof, and the second side of the elbow member 11 may be attached to the drainage tube 12 leading to the reservoir 13, as shown in FIG. 12. The elbow joint 11 may be formed into any desired angle, and preferably is formed into an angle in the range of 40 to 50 degrees. This arrangement allows the drainage tube 12 to extend in any desired direction toward the reservoir 13 in a low profile manner, rather than having the drainage tube 12 extend in linear fashion from the tube connector 8, which may be awkward or cumbersome in some situations or tight spaces.

FIG. 2 illustrates an embodiment of the present invention whereby the ostomy output diversion device is strapped on a person in a typical manner, covering and sealing over the person's stoma or fistula, allowing effluent to exit the stoma or fistula, pass through the ostomy output diversion device, into a drain tube 12 attached to the drain tube connector 8 of the ostomy output device, and into a reservoir 13 for collecting ostomy output.

FIG. 3A illustrates an embodiment of the present invention whereby the ostomy output diversion device has a body support strap 9 and strap mounting ring 10 that fits over the distal end of the outer frame 14, so that the strap is used to secure the ostomy output diversion device to the body during application. FIG. 3B illustrates an embodiment of the present invention whereby the body support strap 9 and strap mounting ring 10 are removable from the ostomy diversion device.

FIG. 4 illustrates an embodiment of the present invention whereby the body support strap 9 is integrally formed with the base ring 2 for securing the ostomy output diversion device to the body during application.

In use, after an ostomy patient has removed a used bag and attachment apparatus and cleaned the skin around the stoma or fistula, the patient places the base ring 2 firmly against his skin so that the adapter 4 is positioned over the stoma or fistula. The patient then extends the adapter 4 inwardly toward the stoma or fistula until the sealing ring 5 is firmly in place around the stoma or fistula and secured in place by the pressure adjustment lock 6, and then affixes the strap ring 10 around the distal portion of the outer frame 14 and secures the strap 9 around his body. The next step includes affixing the drainage tube 12 to the tube connector 8 (or affixing the drainage tube 12 to the elbow joint 11, and the other side of the elbow joint 11 to the tube connector 8), and connects the other end of the drainage tube 12 to a reservoir 13. It should be understood that some of these steps may be combined or performed out of the recited order without departing from the scope or the spirit of the present invention.

This device allows the peristomal skin around the stoma to remain uncovered for extended periods of time, so that it can breathe and potentially be treated with an ointment, salve or other topical medical treatment, for long as the patient desires. Once the ostomy output diversion device is properly secured to the patient's body, the patient's hands can remain free of the device, and may be used for other tasks or activities (or may simply rest) while the device is held in place by the straps 9.

FIGS. 5-8 show another embodiment of the present invention, wherein the strap ring 10 includes a pouch mounting ring 20 on an outer portion thereof. An ostomy pouch 22 may be removably attached to the pouch ring 20 in order to receive effluent from the patient's stoma or fistula while the ostomy output diversion device is properly secured to a patient's body.

FIGS. 9-11 illustrate another embodiment of the present invention, wherein an output adapter 24 may be removably secured to the strap ring 10 (or, alternatively, to a pouch mounting ring 20). The output adapter 24 is attached to a drainage tube, which in turn is operatively attached to a reservoir for receiving effluent from the patient's stoma or fistula.

In another alternate embodiment, the inner tube member may be removable and interchangeable with a disposable cartridge or receptacle, such as a receptacle as described in U.S. Pat. No. 10,130,505, which is hereby incorporated herein by reference, in its entirety. In this embodiment, the disposable receptacle may be inserted into the outer frame member and used to receive the effluent from the stoma or fistula while the ostomy output diversion device is in place on a patient's body. Then, the disposable receptacle containing the effluent may be removed, sealed, and properly disposed of.

In another embodiment, as shown in FIGS. 13-19, an ostomy output diversion device includes a main body member 1 having a base ring 2, support members 16 attached to the base ring 2 on a first end thereof, and an outer frame 14 attached to the support members 16 on a second end thereof. An inner tube 3 is positioned on an inner portion of the outer frame member, and includes a first opening that fits over a stoma or fistula, where the first opening is located generally in a central position with respect to the base ring. A second opening is positioned on a lower portion of the inner tube, and is attached to a drainage adapter for receiving a drainage channel. As in other embodiments described herein, the other end of the drainage channel may be attached to a pouch or reservoir for collecting effluent that flows outwardly from the stoma or fistula, through the first opening in the adapter, and downwardly through the second opening and into the drainage channel. The outer frame 14 defines a centrally located opening on a distal end thereof, which is on an outer portion of the device on an opposite end from the base ring. The centrally located opening in the outer frame member allows a user or health care provider to look therethrough for purposes of aligning the first opening on the adapter with the stoma or fistula on a patient's body. A removable concealing cap 28 may be affixed to the inner tube member 3, as shown in FIGS. 13 and 14, to cover the centrally located opening. Additionally, adjustable tension straps 9 may be affixed to the removable concealing cap 28, and the adjustable tension straps may be used to 1) maintain the removable concealing cap 28 in place on the inner tube member 3, and 2) to provide additional tension to the inner tube member for a snug fit of the inner tube against the skin next to a patient's stoma.

In an embodiment shown in FIG. 20, the concealing cap also includes an odor filter 29 that essentially serves two primary purposes: 1) it releases gases trapped in a user's body as part of the natural digestive processes, and 2) reduces or eliminates the odors that are associated with such gases. In embodiments that do not include an odor filter, an air valve or gas bleed valve may be incorporated into the system for releasing gases. Odor filters are widely available commercially. For example, bamboo air purifier deodorizing carbon charcoal filters are sold commercially for use with diaper pails by Ninja Mama on Amazon.com. Bush Systems sells carbon odorless cloth diaper pail filters on Amazon.com, and Arm and Hammer sells nursery fresheners that include baking soda and assorted scents. Any of these types of odor air filters may be used in conjunction with the present invention, as well as any other suitable air filters.

It should be understood that other structural arrangements may be used without departing from the spirit or scope of the present invention. For instance, it is conceived that one, two or more support members may be used, rather than the four support members shown in the Figures, in order to provide easier access to the peristomal skin while the ostomy output diversion device is strapped onto a patient's body.

In another embodiment, as shown in FIGS. 21-26, an ostomy output diversion device includes a main body member 1 having a base ring 2, support members 16 attached to the base ring 2 on a first end thereof, and a cylinder guide 107 attached to the support members 16 on a second end thereof. The diverter cylinder 103 is inserted into the cylinder guide 107, positioned on an inner portion of the outer frame member, and includes a first opening defined by a sealing ring 105 that fits over a stoma or fistula, where the first opening is located generally in a central position with respect to the base ring 2.

A second opening, a vertical output channel 125, is positioned on a lower portion of the diverter cylinder 103, with a pouch or reservoir connector clip 133, is used to attach an ostomy pouch or reservoir 22 for receiving stoma output drainage.

A third opening is positioned on the diverter cylinder 103 on an opposed side from the base ring 2, and is adapted to accommodate a removable cover 28, which can be removed to assist the patient or a caregiver with aligning the sealing ring 105 over the stoma.

The diverter cylinder 103 moves inwardly and outwardly, within the cylinder guide 107, and is incrementally or infinitely adjustable in linear fashion in order to allow movement within the cylinder guide 107 and diverter cylinder 103. Movement of the diverter cylinder 103 is based on a predefined parameter, encompassing the measurement of the diverter cylinder 103, from the sealing ring 105 to the removable cover 28, determined by the patient's body type, and initiated by the tension spring 135, placed over a tension spring rod 134, which is attached to a tension top bracket 131 and located inside a tension spring housing 130.

The tension spring assembly is comprised of the tension spring 135 compressed between the stop end of the tension spring rod 134 and the upper closed end of the tension spring housing 130. In use, when the base ring 2 is placed in the proper position against a patient's skin, the sealing ring 105 is biased inwardly toward the skin around the stoma to create a preferably tight seal therearound. This biasing force is achieved as the attached tension spring rod 134, compresses the tension spring 135 to create the inwardly biased force used to secure seal between the sealing ring 105 and the patient's body. The tension top bracket 131 can preferably swivel in a full rotation, allowing access to install the diverter cylinder 103 into the cylinder guide 107, or conversely, to remove the diverter cylinder 103 from the cylinder guide 107.

Figure 24:
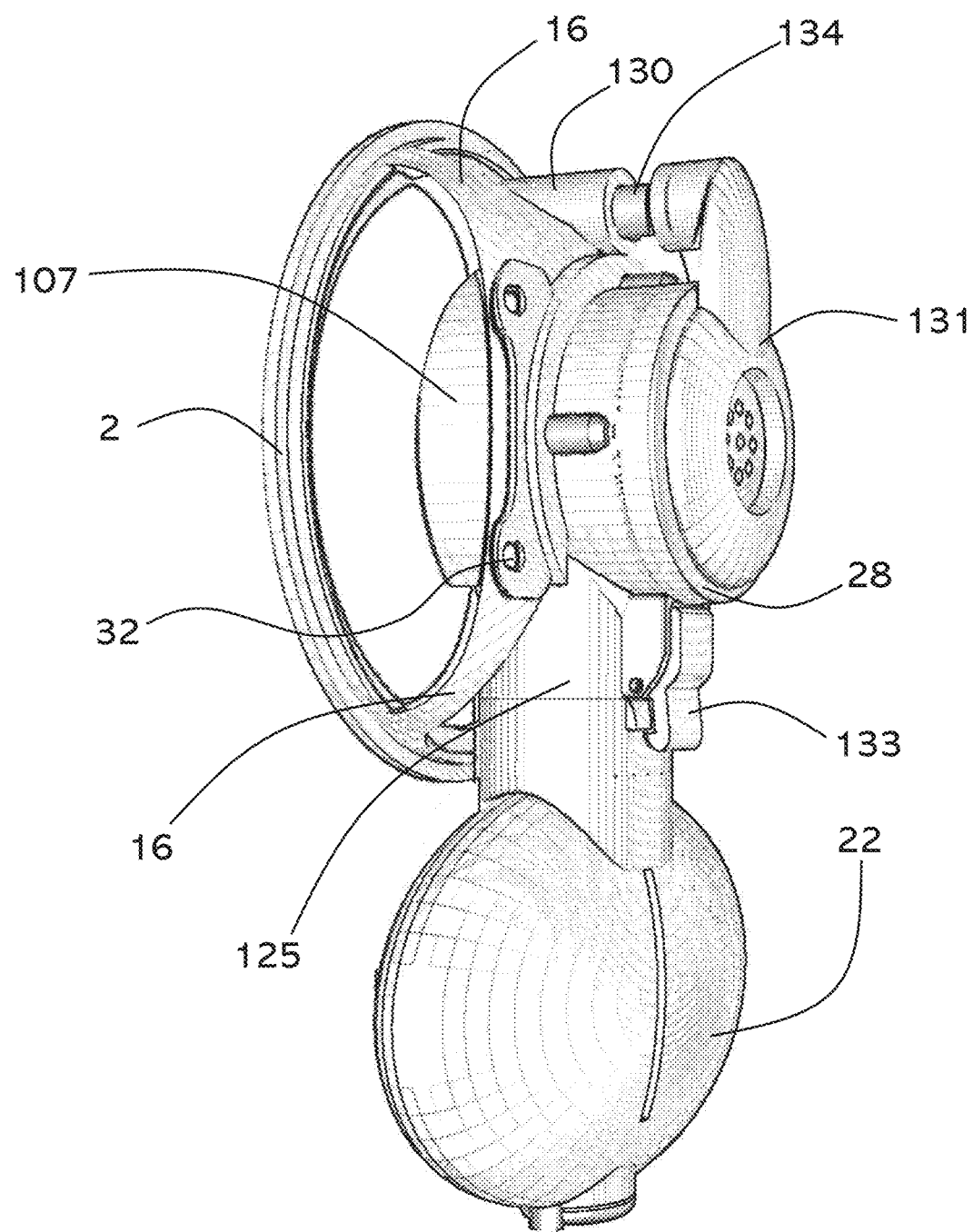
FIG. 24 is a perspective view of the embodiment of the ostomy output device shown in FIG. 21, further including an ostomy pouch attached to the bottom portion of the vertical output channel.
Figure 25:
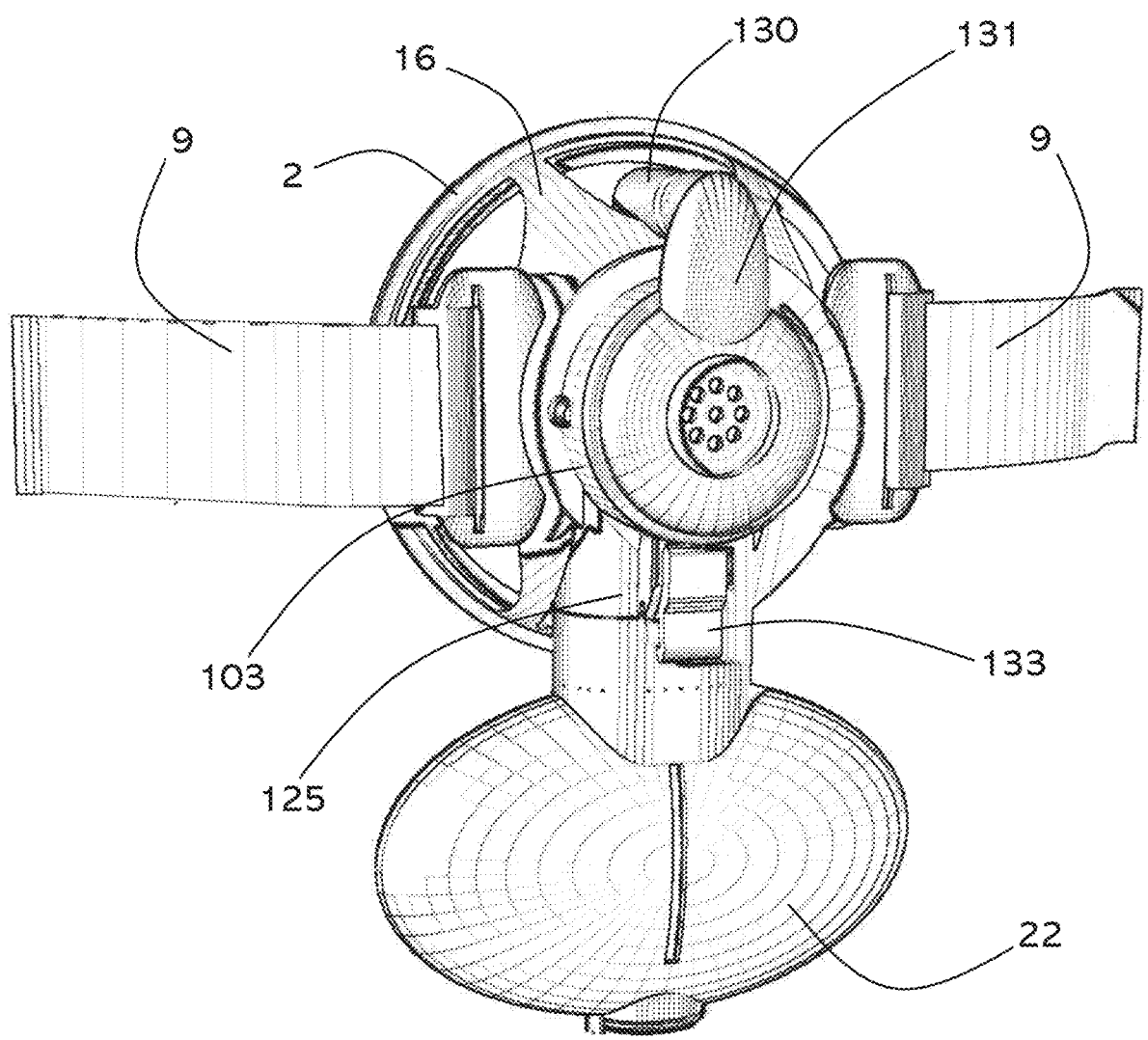
FIG. 25 is a front perspective view of another embodiment of an ostomy output device, wherein a pair of straps are attached to an outer portion of the diverter cylinder, and wherein the concealing cap includes an air filter therein.

In another embodiment, the ostomy output diversion device includes a removable body support strap 9, used to secure the ostomy output diversion device to the body during application. The removable body support strap 9 may be affixed to the body strap connectors 32, which are preferably mounted on an outer portion of the diverter cylinder 103, as shown in FIGS. 24 and 25. Alternatively, the strap 9 may be affixed to other portions of the device. Any suitable strap means may be used to attach the device to a patient's body, so long as the device, and specifically the sealing ring 105 are held firmly in place against the patient's skin, in order to prevent any effluent from leaking therefrom.

Figure 26:
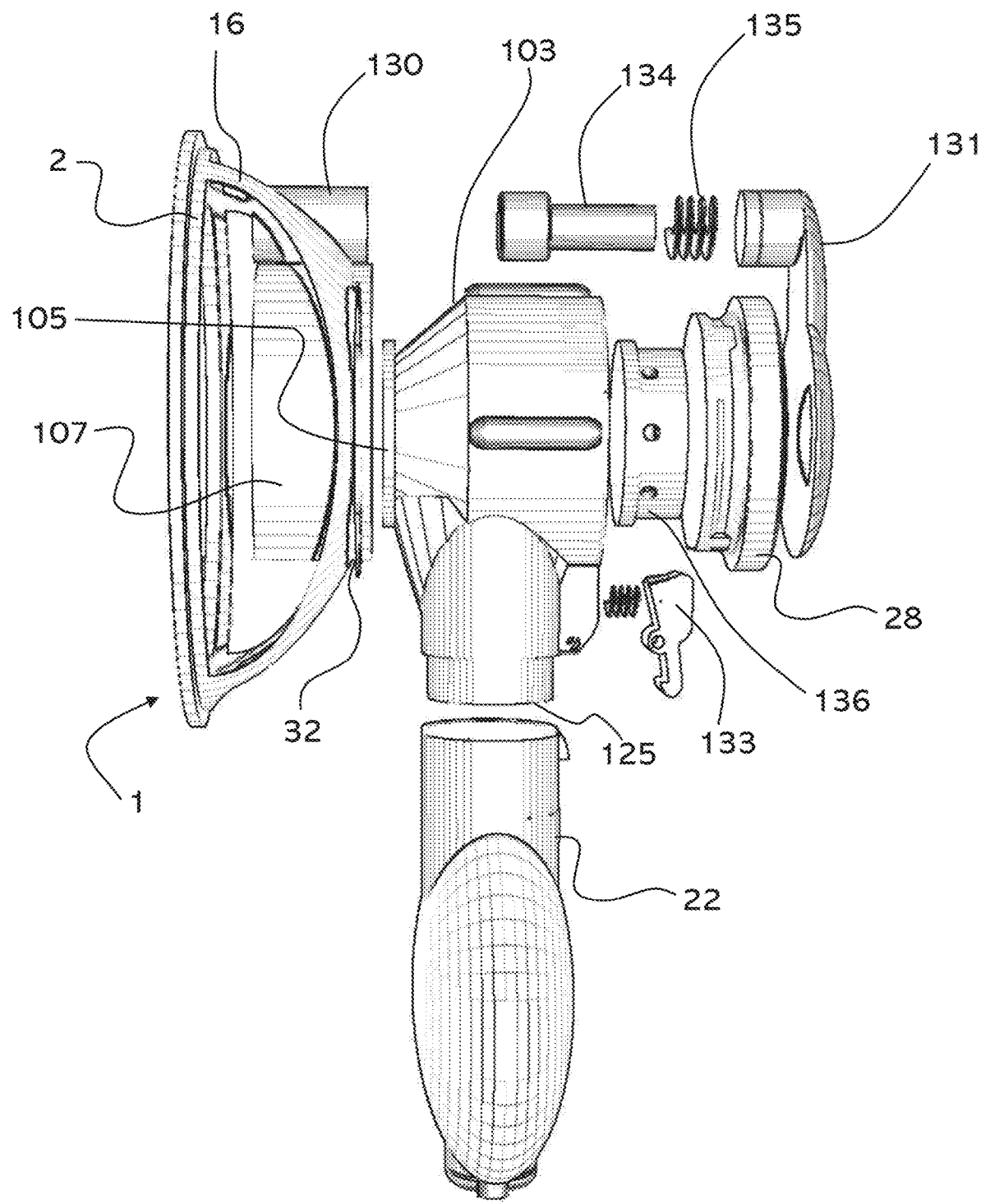
FIG. 26 is an exploded view of the embodiment of the ostomy output device shown in FIG. 21 showing the outer frame member and base ring assembly, the diverter cylinder, the concealing cap and tension mechanism including the spring-loaded tension spring rod, an ostomy pouch at a bottom portion thereof, and a pouch connector clip for connecting the ostomy pouch to the vertical output channel.

As in other embodiments described herein, the lower end of the vertical output channel 125 may be attached to a pouch or reservoir 22 for collecting effluent that flows outwardly from the stoma or fistula, through the first opening in the diverter cylinder 103, and downwardly through the second opening and into the vertical output channel 125. The diverter cylinder 103 preferably defines a centrally located opening on a distal end thereof, on an opposed side from the first opening, which is on an outer portion of the device on an opposite end from the base ring, so that the centrally located opening is oriented in linear fashion to line up with the first opening and sealing ring 105. The centrally located opening in the diverter cylinder 103 allows a user or health care provider to look therethrough for purposes of aligning the first opening and the sealing ring 105 with the stoma or fistula on a patient's body. A removable concealing cap 28 may be affixed to cover the centrally located opening on the diverter cylinder 103, as shown in FIGS. 25 and 26. Additionally, adjustable tension straps 9 may be affixed to the removable concealing cap 28, and the adjustable tension straps may be used to 1) maintain the removable concealing cap 28 in place on the diverter cylinder 103, and 2) provide additional tension to the cylinder guide 107 for a snug fit of the sealing ring 105 against the skin next to a patient's stoma.

In an embodiment shown in FIGS. 24 and 25, the concealing cap 28 also includes an odor filter 29 that essentially serves two primary purposes: 1) it releases gases trapped in a user's body as part of the natural digestive processes, and 2) reduces or eliminates the odors that are associated with such gases. In this embodiment, the concealing cap may define a series of holes therein for air to flow through. The concealing cap preferably includes a filter housing 136 for retaining a removeable and replaceable filter therein.

Optionally, and filter cap may be used to maintain the filter within the filter housing, and the filter cap may include a series of holes to facilitate air flow therethrough.

In embodiments that do not include an odor filter, an air valve or gas bleed valve may be incorporated into the system for releasing gases. Any suitable odor filter may be used, as described herein, and as recognized by those having skill in the art.

Although the present invention has been described in considerable detail with reference to certain preferred versions thereof, other versions are possible. Therefore, the spirit and scope of the appended claims should not be limited to the description of the preferred versions contained herein. All features disclosed in this specification may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. An ostomy output diversion device comprising:
a base ring;
an outer frame member attached to said base ring, said outer frame including a cylinder guide;
a diverter cylinder that is adapted to movably slide into said cylinder guide so that said diverter cylinder is configured to move inwardly and outwardly within said cylinder guide, said diverter cylinder including a first opening for receiving effluent from a stoma and includes a vertical output channel for drainage of effluent;
wherein said diverter cylinder defines a centrally located opening on an opposed side from said first opening;
a removable concealing cap adapted to be received in said centrally located opening;
a tension top bracket attached to said removable concealing cap, said tension top bracket including a spring loaded tension spring rod:
wherein said outer frame member includes a tension spring housing for removably receiving a distal end of said tension spring rod, so that the spring loaded tension spring rod urges said outer frame member away from said diverter cylinder; and
said vertical output channel being adapted to receiving a removable ostomy pouch.

2. The ostomy output diversion device set forth in claim 1, wherein said concealing cap includes a filter for reducing odor.

3. The ostomy output diversion device set forth in claim 1, further comprising a pouch connector clip attached to said diverter cylinder for removably securing said ostomy pouch to said vertical output channel.

4. The ostomy output diversion device set forth in claim 1, further including elastic tension straps attached to said diverter cylinder.

* * * * *